US008822198B2

(12) United States Patent
Schlatter et al.

(10) Patent No.: US 8,822,198 B2
(45) Date of Patent: Sep. 2, 2014

(54) METHOD FOR OPTIMIZING A BIOPHARMACEUTICAL PRODUCTION PROCESS

(75) Inventors: Stefan Schlatter, Achstetten (DE); Christian Sauter, Ulm (DE); Eugen Probst, Ummendorf (DE); Franz Wiedemann, Altusried (DE); Carina Guelch, Freiburg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/514,692

(22) PCT Filed: Dec. 17, 2010

(86) PCT No.: PCT/EP2010/070042
§ 371 (c)(1),
(2), (4) Date: Aug. 20, 2012

(87) PCT Pub. No.: WO2011/073377
PCT Pub. Date: Jun. 23, 2011

(65) Prior Publication Data
US 2013/0244275 A1    Sep. 19, 2013

(30) Foreign Application Priority Data

Dec. 18, 2009 (EP) .................................. 09179954
Apr. 28, 2010 (EP) .................................. 10161272

(51) Int. Cl.
*C12N 1/00* (2006.01)
*C12N 5/02* (2006.01)

(52) U.S. Cl.
USPC ..................... 435/256.8; 435/404; 435/431

(58) Field of Classification Search
USPC ........................................ 435/256.8, 404, 431
See application file for complete search history.

(56) References Cited

U.S. PATENT DOCUMENTS 3,871,967 A * 3/1975 Abdou et al. .............. 435/253.6
5,597,400 A * 1/1997 Nonomura et al. ............... 71/28
6,338,964 B1 * 1/2002 Matanguihan et al. ....... 435/404

FOREIGN PATENT DOCUMENTS

| WO | 9110726 A1 | 7/1991 |
| WO | 9738090 A1 | 10/1997 |
| WO | 0152647 A1 | 7/2001 |
| WO | 2010017338 A1 | 2/2010 |

OTHER PUBLICATIONS

Google search for "glycerophosphate pentahydrate," p. 1 of search results, printed from the Internet on Nov. 20, 2013.*
Williamson et al., Use of a new buffer in the culture of animal cells, The Journal of General Virology, Mar. 1968, vol. 2 No. 2, pp. 309-312, XP002601061.
Hasegawa et al., Culturing method providing algae contg docosahexa:enoic acid—comprises culturing in sodium chloride-enriched medium, WPI/Thomson, Mar. 20, 1995, vol. 1995 No. 20, XP002589921, Abstract only.

(Continued)

*Primary Examiner* — Rosanne Kosson
(74) *Attorney, Agent, or Firm* — Michael P. Morris; Alan R. Stempel

(57) ABSTRACT

The invention describes the development of a new buffer system for cell culture media for establishing a $CO_2$ regulation in the bioreactor with eukaryotic cells. This technology makes it possible to obtain $CO_2$ regulation for process control, process optimization and scaling. In addition, the invention describes a specific cell culture medium with specific buffer substances.

11 Claims, 22 Drawing Sheets

(56) References Cited

OTHER PUBLICATIONS

Matsutani et al., Serum-free synthetic medium used for cell culture—comprising medium contg. mixt. of eagle mem and rpm11640, and additives, with their osmotic pressure adjusted, WPI/Thomson, Feb. 4, 1986, vol. 1986 No. 11, XP002589922, Abstract only.

Zhu et al., Effects of elevated pCO2 and osmolality on growth of CHO cells and production of antibody-fusion protein B1: a case study, Biotechnology Progress, Jan. 1, 2005, vol. 21 No. 1, pp. 70-77, XP002536931.

Laird et al., Rapid, direct tissue culture test for toxigenicity of Corynebacterium dipheriae, Applied Microbiology, May 1973, vol. 25 No. 5, pp. 709-712, XP002601062.

Gnoth et al., Control of cultivation processes for recombinant protein production: a review, Bioprocess and Biosystems Engineering, Oct. 5, 2007, vol. 31 No. 1, pp. 21-39, XP019564177.

Robinson et al., Optimization of a fed-batch process for production of a recombinant antibody, Annals of the New York Academy of Sciences, Nov. 30, 1994, vol. 745, pp. 285-296, XP009021037.

International Serch Report, Form PCT/ISA/210, for International Application PCT/EP2010/070042, Date of mailing May 6, 2011.

\* cited by examiner

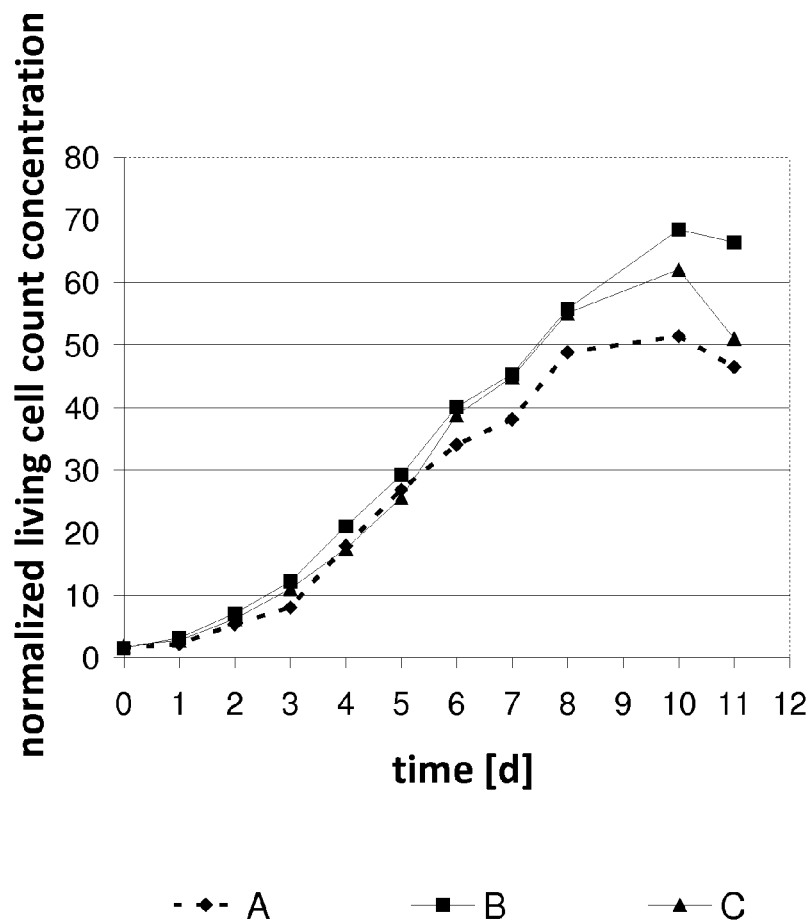

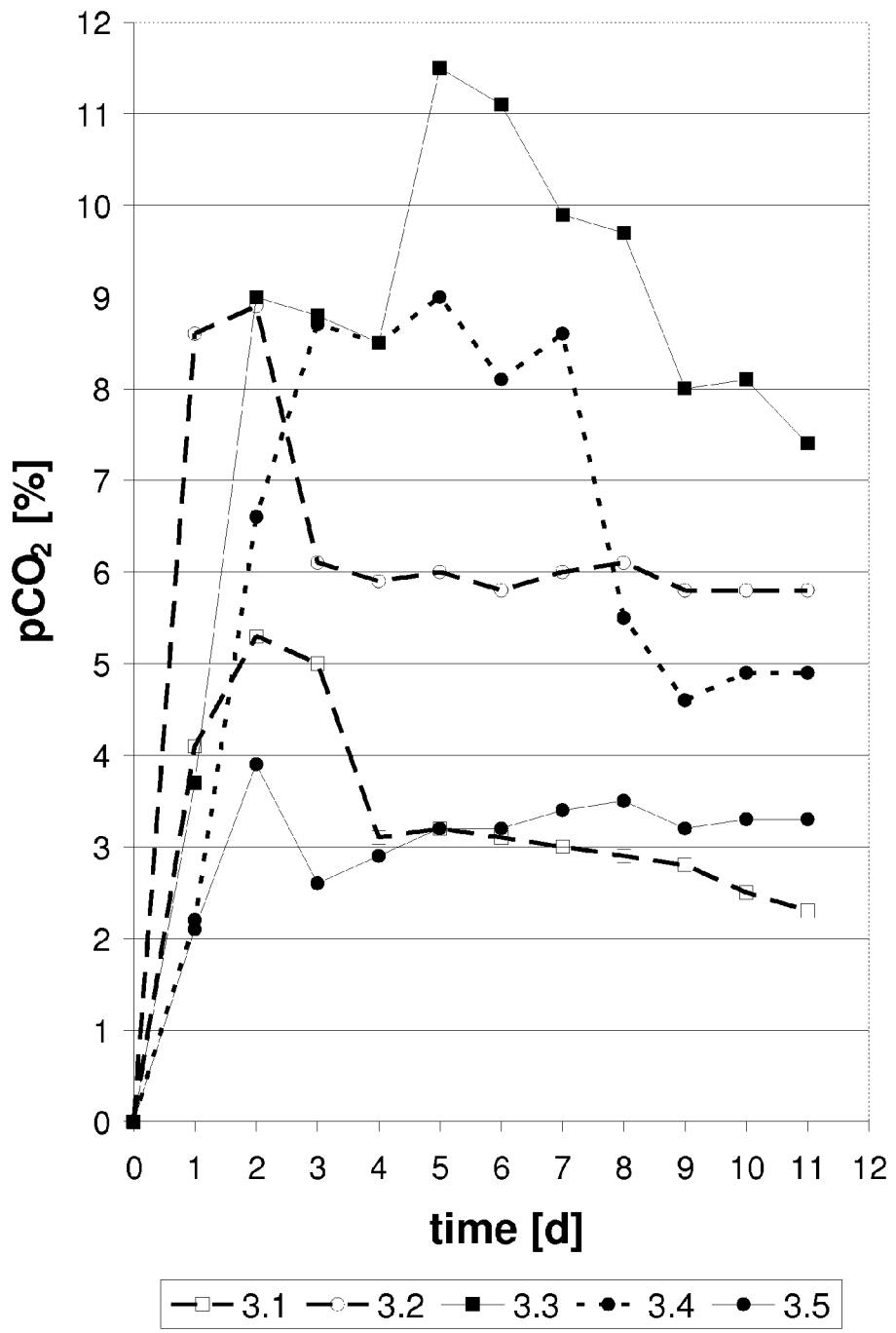

METHOD FOR OPTIMIZING A BIOPHARMACEUTICAL PRODUCTION PROCESS

BACKGROUND TO THE INVENTION

1. Technical Field

The invention relates to the field of biopharmaceutical process development with eukaryotic cells that produce recombinant protein of interest. In particular, the invention relates to a method of optimising the management of the process, which comprises using an $Na_2CO_3$ and $NaHCO_3$ free or reduced medium in conjunction with a $pCO_2$ regulation.

2. Background

Biopharmaceutical process development is confronted with the requirement of providing ever higher titres for the production of therapeutic proteins, particularly antibodies for clinical (toxicological) studies with tight deadlines, or for supplying the market.

Within the scope of these time constraints, expression systems have to be designed, stable production cell clones have to be generated and selected for production (e.g. CHO cells, hybridomas, BHK or NSO cells), scalable biopharmaceutical production processes have to be designed, comprising media optimisation and process control. All this has to be addressed so that the specific productivity (=specific product formation rate) and the titres achieved (product yield) are maximised, to enable the processes to be run robustly and reproducibly in plants of different sizes. In recent years enormous increases in product titres have been achieved in recombinant eukaryotic cell systems. Thus, for example, product concentrations of more than 5 g of immunoglobulin/L in Chinese Hamster Ovary (CHO) cells have been achieved. Progress in molecular biology and cell biology includes genetic cell line development and changes, development of media, and "in-process" control strategies such as the addition of nutrients ("feed") have made this possible, inter alia. However, the productivities of eukaryotic cell systems, particularly mammalian cell systems, do not approach those of prokaryotic cell systems and therefore the further optimisation of, in particular, process control during fermentation and the optimisation of the fermentation medium is still a requirement.

One particular requirement is the control of the oxidative metabolism.

All cells produce $CO_2$ within the scope of oxidative metabolism and require $HCO_3^-$ for a variety of related transport processes. Elevated $CO_2$ contents, which may occur, for example, when there is strong growth, lower the pH, and this can be neutralised by an increased sodium hydrogen carbonate content. Thus, sodium hydrogen carbonate is both a buffer substance and an essential nutrient. Sodium hydrogen carbonate is described as an essential nutrient in, among others, the textbook by Lindl, Toni; Gstraunthaler Gerhard (2002): Zell- und Gewebekultur [Cell and Tissue Culture], 5th edition, Spektrum Akademischer Verlag Heidelberg, p. 93, Point 4.4.3, or in Ling, C. T. et al (1968): Chemically characterized concentrated corodies for continuous cell culture (The 7C's culture media), in Experimental Cell Research Nr. 52, p. 469-489.

Moreover, hydrogen carbonate plays a part in the citric acid cycle, in the pH regulation of the whole body as well as individual cells, and regulation of their volume. The membranes of mammalian cells contain transport proteins for hydrogen carbonate to assist with transmembrane transport. Whereas $CO_2$ is capable of penetrating through the lipid bilayer by diffusion, $HCO_3^-$ is charged and can only pass through the membrane with the aid of specific transport proteins. On the basis of the acid-base properties of $CO_2/HCO_3^-$, the expulsion of $CO_2$ from the cell results in an alkalisation of the cell, whereas the efflux of $HCO_3^-$ acidifies the cell (Casey Joseph. R. (2006): Why bicarbonate? in Biochem. Cell Biol. No. 84, S. 930-939).

SUMMARY OF THE INVENTION

In order to achieve the goal of being able to regulate $CO_2$ completely in the fermentation process, $HCO_3^-$ or $CO_3^{2-}$ ions e.g. originating from sodium hydrogen carbonate buffer have to be replaced by an alternative buffer substance. At present, as shown in the following chemical equation, $CO_2$ may be formed during the reaction with lactic acid (LA):

$$NaHCO_{3(aq)} + LA_{(aq)} \rightarrow \text{Na-lactate}_{(aq)} + CO_{2(aq)} + H_2O \quad \text{(equ. 1)}$$

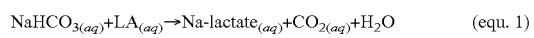

Currently, the regulation of the pH value is carried out with $Na_2CO_3$ solution which, as shown in equation 2, can break down to form $NaHCO_3$. The product $NaHCO_3$ from equation 2 in turn becomes the educt in equation 1.

$$Na_2CO_{3(aq)} + H_2O \rightarrow NaHCO_{3(aq)} + OH^- + Na^+ \quad \text{(equ. 2)}$$

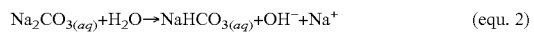

As described above, cells cannot exist without $HCO_3^-$ as it is essential for important cell functions. It therefore appears impossible to dispense entirely with $HCO_3^-$—originating from the buffer substance $NaHCO_3$ or from the pH regulating agent $Na_2CO_3$ solution. However, the cells have additional sources of bicarbonate.

$$CO_2 + H_2O \rightleftharpoons H_2CO_3 \rightleftharpoons HCO_3^- + H^+ \quad \text{(equ. 3)}$$

$$CO_2 + H_2O \xrightarrow{\text{carbonic anhydrase}} H_2CO_3 \rightleftharpoons HCO_3^- + H^+ \quad \text{(equ. 4)}$$

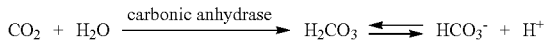

Whereas equ. 3 takes place spontaneously, e.g. when $CO_2$ gas is introduced, the reaction in equ. 4 is additionally assisted by the intracellular enzyme carbon anhydrase. Thus the cell can if necessary synthesise its own bicarbonate from $H_2O$ (present in the cell culture medium) and $CO_2$ (which is for example added in as a gas or is a by-product from the cell cycle).

The first step to regulating $pCO_2$ in the fermentation system is the search for alternative buffer substances for sodium hydrogen carbonate, $NaHCO_3$. With the standard medium/$NaHCO_3$-containing standard buffer an equilibrium is formed between $CO_2$ (gas) and $CO_2$ (aq), which influences the pH of the cell culture.

The new, alternative buffer substance, wholly or partially replacing $HCO_3^-$ or $CO_3^{2-}$ ions originating for example from sodium hydrogen carbonate, must have a good buffer activity and not adversely affect the cell culture. Also, the performance and product formation (titre) must remain at least at the same high level. For example, a case might arise in which the new buffer substance does indeed exhibit good buffer characteristics but has a toxic effect on the cell or damages the product secreted extracellularly. Furthermore, undesirable reactions may occur with the other constituents of the cell culture medium and lower the vitality rates, for example. A lowering of vitality means more dead cells in the culture, which release harmful cell contents such as proteases into the fermentation liquor. As a second priority the new buffer substance should be inexpensive, should not require any special treatment for storage and handling and should be obtainable from a number of suppliers.

The second step/another step towards the regulating of $pCO_2$ in the fermentation system is to establish an optimum $CO_2$ profile which has a positive effect on the metabolism of the cells, in that fewer toxic metabolic products are formed (lactate, ammonium) and/or the additions of acid and alkali for regulating the pH are minimised. The optimum profile is adapted to the corresponding growth phase (initial growth phase, growth phase, drying-off phase) with the aim of shortening the initial growth phase, lengthening the growth phase and increasing the specific product formation rate during the growth phase. The $CO_2$ profile selected thus serves to control the process in a deliberate manner and is divided into a number of regulating sections: a low $pCO_2$ in the initial growth phase (<10% tbd, preferably 3-8% or 3-5%, particularly preferably 5% or 3%) promotes a faster start-up of the cells, a moderate $pCO_2$ (<12% tbd, preferably 5-11%) in the growth phase promotes a high growth rate and better metabolism, thus forming less lactate than at a higher $pCO_2$, whereas a slightly increased or high $pCO_2$ (>5%, >8%, >15% tbd, preferably 5-10%) in the drying-off phase counteracts the addition of alkali and thus helps to lower the osmotic pressure and hence to extend the productivity phase.

Another important aspect of the invention is the scalability and in particular the transferability of a process across the different fermenter volumes. In conventional fermentation systems the $pCO_2$ depends on the equipment used and the scale and traditionally increases as the scale is increased. It is not possible to counteract this phenomenon without at the same time altering the metabolism of the cell, as in conventional systems the $pCO_2$ is coupled to the gas supply and the pH regulation. By uncoupling the $pCO_2$ regulation from the regulation of the pH and the gas supply (more accurately the regulation of $pO_2$) by means of the buffer system described in the present invention, combined with the $pCO_2$ regulation, an increase in scale can be achieved easily and without fundamentally changing the fermentation characteristics (=performance), while at the same time the regulation of the gas supply (more accurately $pO_2$), pH and $pCO_2$ are each separately transferred and thus ensure a comparable cell culture performance on all the fermentation scales.

The present invention achieves this objective by providing a method of optimising a biopharmaceutical production process and comprises the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, the said cell culture medium containing the following buffer component:
(i)   N-tris(hydroxymethyl)methyl-2-aminoethanesulphonic acid (C6H15NO6S, TES) and/or
(ii)   sodium-β-glycerophosphate-pentahydrate (C3H7Na2O6P×5H2O, Sod-β)
c) regulating the pH by means of a non-$CO_2$-forming acid and/or alkali,
while during the bioprocess the $pCO_2$ is regulated with $CO_2$, $O_2$, $N_2$ and/or a supply of air or using the speed of the stirrer, the regulation being characterised in that in the initial growth phase a lower $pCO_2$ is selected. Preferably, the $pCO_2$ is regulated with $CO_2$ and/or $N_2$. Moreover, the invention relates to a cell culture medium which contains 12 mmol/L or less of $HCO_3^-$ or $CO_3^{2-}$ ions, the said cell culture medium containing the following buffer components:
(i)   N-tris(hydroxymethyl)methyl-2-aminoethanesulphonic acid (C6H15NO6S, TES) and/or
(ii)   sodium-β-glycerophosphate-pentahydrate (C3H7Na2O6P×5H2O, Sod-β).

In the regulated fermentation in the bioreactor, the pH is regulated by the introduction of CO2 gas and the addition of liquid alkali, e.g. $Na_2CO_3$. However, to enable the pH to be regulated independently of $pCO_2$, the buffer system and the associated pH regulation must be provided using agents that do not release $CO_2$. Only by eliminating $CO_2$-forming buffer and acid/base is it possible to achieve independent regulation of DO (dissolved oxygen, $pO_2$) and $pCO_2$. In addition, both the buffer system and the acid/base contribute crucially to the osmolality (osmo). The $CO_2$ independent buffer system with acid/base was therefore developed specially for osmoreduction. The $pCO_2^-$ regulation contributes to the optimisation of bioprocesses, as an additional regulating variable, and is used to increase the process performance by optimising the $pCO_2$ profile, improving the reproducibility and the scalability.

One advantage of the method according to the invention is a significant improvement in the specific product formation rate/specific productivity. Moreover, the product quality, the fermentation time and the cell metabolism can generally be positively influenced. This means, for example, that the fermentation time in a fed batch method can be extended while at the same time achieving a high product yield.

The implementation of another regulating variable ($pCO_2$) allows improved process optimisation. The pH profile, the temperature profile, the speed profile, the $O_2$ profile and the $pCO_2$ profile can be optimised independently of one another. The optimised conditions then contribute significantly to increased reproducibility and transferability to different bioprocesses and scales of production. It is important here that only by uncoupling the three regulating variables mentioned above, by introducing a separate $pCO_2$ regulation with a new buffer system, is it possible to achieve an independent transfer of scale; in conventional systems the 3 regulating variables all affect one another to a greater or lesser extent depending on scale. Therefore, in conventional systems, it is not possible to transfer these 3 regulating variables identically.

The osmo-reduced acid-base buffer system leads to an increased cell vitality, increases the cell-specific productivity and allows a further increase in productivity by extending the process time. Preferred acids and alkalis for the pH regulation according to the invention are NaOH (sodium hydroxide solution), acetic acid, phosphoric acid, sulphuric acid and hydrochloric acid. Hydrochloric acid, phosphoric acid and sulphuric acid are preferred. Sulphuric acid is a particularly preferred acid.

Another benefit of the new $NaHCO_3$-free medium can be found in the field of analysis: in some experiments in cell culture technology it is important to determine the carbon dioxide formation rate (CER). Eliminating the $CO_2$ sources buffer, base and acid makes it possible in the first place to achieve a carbon balance, for example by exhaust gas analysis and this carbon balance is or can be used to optimise the process.

The carbon balancing is carried out by detection, e.g. by exhaust air analysis. The new regulating strategy permits an exact carbon balancing (for example CER) which is used as an optimisation tool. The carbon dioxide formation rate indicates the amount of $CO_2$ formed by the cells in a liter of culture liquor in one hour. If the operator is obliged to use a cell culture medium that is buffered by bicarbonate, peculiarities arise in the determination of the carbon dioxide formation rate. In the physiological pH range, in the total carbonate there is an equilibrium between $CO_2$ and $HCO_3^-$, which is influenced by the pH. To obtain a balance, the gas composition is analysed as it is added to and as it is removed from the fermenter. Hitherto it has been difficult to obtain a balance in media NaHCO$_3$, as the actual storage effect of the cell culture liquor is unknown. The new medium free from HCO$_3^-$ or CO$_3$, which is optimally adapted to the cell, opens up new possibilities.

Another benefit of the invention is the improvement in the reproducibility of bioprocesses. This means that, in repeated fermentation runs in different scalings with a controlled pCO$_2$, comparable results are obtained in terms of final titre, cell count, metabolism, etc. In fermentation runs that are not pCO$_2$-controlled, these parameters may fluctuate considerably in some cases from one fermentation run to another, particularly when the scaling is different.

DESCRIPTION OF THE FIGURES

An example of the construction of the bioreactor used is described in Example 3. However, the construction of the bioreactor is variable in principle, so as to meet different requirements. For example, a riser tube may be omitted and instead an additional probe may be installed or further/other solutions may be added automatically by means of hose pumps.

Figure 1:
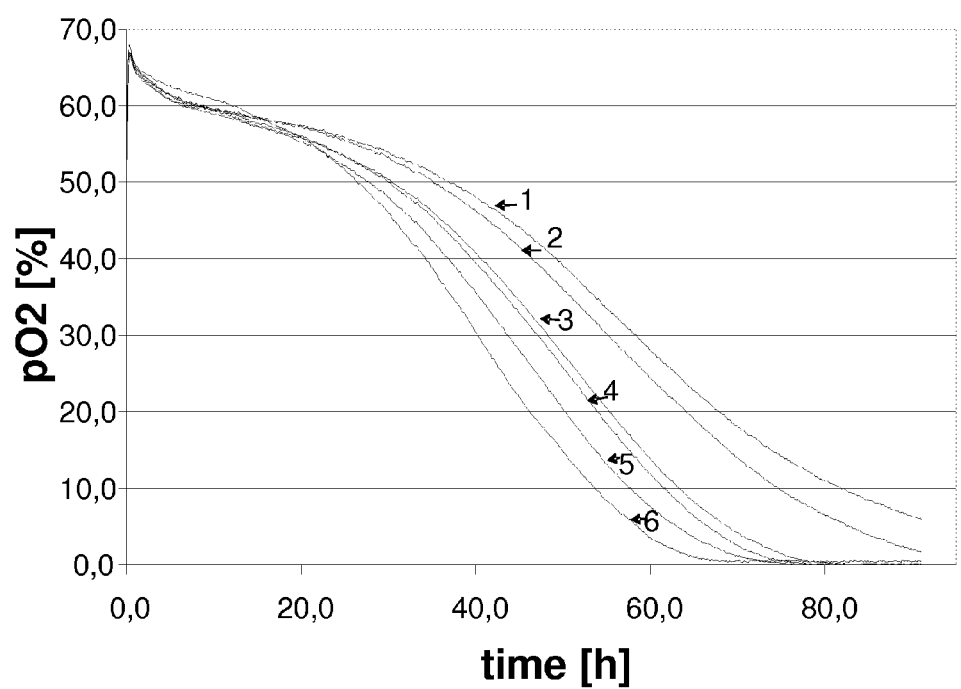
FIG. 1 COMPARISON PO2 [%] WITH VARIABLE NAHCO3 CONCENTRATION

Buffer conditions:
Curve 1=Medium A NaHCO$_3$-free+ZERO NaHCO$_3$ (completely NaHCO$_3$-free)
Curve 2=Medium A NaHCO$_3$-free+1 mM NaHCO$_3$
Curve 3=Medium A NaHCO$_3$-free+4 mM NaHCO$_3$
Curve 4=Medium A NaHCO$_3$-free+8 mM NaHCO$_3$+20 mM HEPES
Curve 5=Medium A NaHCO$_3$-free+8 mM NaHCO$_3$
Curve 6=Medium A NaHCO$_3$-free+36 mM NaHCO$_3$ (control)

FIG. 2 BUFFER SCREEN

A: Buffer screen with a high pCO2 profile
SF01=Medium NaHCO$_3$-free with HEPES buffer 100 mM (1/2)
SF02=Medium NaHCO$_3$-free with HEPES buffer 100 mM (2/2)
SF03=Medium NaHCO$_3$-free with HEPES buffer 60 mM (1/2)
SF04=Medium NaHCO$_3$-free with HEPES buffer 60 mM (2/2)
SF05=Medium NaHCO$_3$-free with MOPS buffer 100 mM (1/2)
SF06=Medium NaHCO$_3$-free with MOPS buffer 100 mM (2/2)
SF07=Medium NaHCO$_3$-free with MOPS buffer 50 mM (1/2)
SF08=Medium NaHCO$_3$-free with MOPS buffer 50 mM (2/2)
SF09=Medium NaHCO$_3$-free with Sod-β 50 mM (1/2)
SF10=Medium NaHCO$_3$-free with Sod-β 50 mM (2/2)
SF11=Medium NaHCO$_3$-free with Sod-β 25 mM (1/2)
SF12=Medium NaHCO$_3$-free with Sod-β 25 mM (2/2)
SF13=Medium NaHCO$_3$-free with TES 80 mM (1/2)
SF14=Medium NaHCO$_3$-free with TES 80 mM (2/2)
SF15=Medium NaHCO$_3$-free with TES 40 mM (1/2)
SF16=Medium NaHCO$_3$-free with TES 40 mm (2/2)
SF17=Medium NaHCO$_3$-free with Trizma base 50 mM (1/2)
SF18=Medium NaHCO$_3$-free with Trizma base 50 mM (2/2)
SF19=Medium NaHCO$_3$-free with Trizma base 100 mM (1/2)
SF20=Medium NaHCO$_3$-free with Trizma base 100 mM (2/2)
SF21=Medium A (control) (1/2)
SF22=Medium A (control) (2/2)
SF23=Medium A Blank (=Medium A MOPS-free, NaHCO$_3$-free) (1/2)
SF24=Medium A Blank (=Medium A MOPS-free, NaHCO$_3$-free) (2/2)
SF49=Medium NaHCO$_3$-free with HEPES buffer 60 mM+NaHCO$_3$ 8 mM (1/1)
SF50=Medium NaHCO$_3$-free with MOPS buffer 50 mM+NaHCO$_3$ 8 mM (1/1)
SF51=Medium NaHCO$_3$-free with Sod-β 25 mM+NaHCO$_3$ 8 mM (1/1)
SF52=Medium NaHCO$_3$-free with TES buffer 40 mM+NaHCO$_3$ 8 mM (1/1)
SF53=Medium NaHCO$_3$-free with Trizma base buffer 50 mM+NaHCO$_3$ 8 mM (1/1)

B: Buffer screen with low pCO2 profile
SF25=Medium NaHCO$_3$-free with HEPES buffer 100 mM (1/2)
SF26=Medium NaHCO$_3$-free with HEPES buffer 100 mM (2/2)
SF27=Medium NaHCO$_3$-free with HEPES buffer 60 mM (1/2)
SF28=Medium NaHCO$_3$-free with HEPES buffer 60 mM (2/2)
SF29=Medium NaHCO$_3$-free with MOPS buffer 100 mM (1/2)
SF30=Medium NaHCO$_3$-free with MOPS buffer 100 mM (2/2)
SF31=Medium NaHCO$_3$-free with MOPS buffer 50 mM (1/2)
SF32=Medium NaHCO$_3$-free with MOPS buffer 50 mM (2/2)
SF33=Medium NaHCO$_3$-free with Sod-β 50 mM (1/2)
SF34=Medium NaHCO$_3$-free with Sod-β 50 mM (2/2)
SF35=Medium NaHCO$_3$-free with Sod-β 25 mM (1/2)
SF36=Medium NaHCO$_3$-free with Sod-β 25 mM (2/2)
SF37=Medium NaHCO$_3$-free with TES 80 mM (1/2)
SF38=Medium NaHCO$_3$-free with TES 80 mM (2/2)
SF39=Medium NaHCO$_3$-free with TES 40 mM (1/2)
SF40=Medium NaHCO$_3$-free with TES 40 mM (2/2)
SF41=Medium NaHCO$_3$-free with Trizma base 50 mM (1/2)
SF42=Medium NaHCO$_3$-free with Trizma base 50 mM (2/2)
SF43=Medium NaHCO$_3$-free with Trizma base 100 mM (1/2)
SF44=Medium NaHCO$_3$-free with Trizma base 100 mM (2/2)
SF45=Medium A (control) (1/2)
SF46=Medium A (control) (2/2)
SF47=Medium A Blank (=Medium A MOPS-free, NaHCO$_3$-free) (1/2)
SF48=Medium A Blank (=Medium A MOPS-free, NaHCO$_3$-free) (2/2)
SF54=Medium NaHCO$_3$-free with HEPES buffer 60 mM+NaHCO$_3$ 8 mM (1/1)
SF55=Medium NaHCO$_3$-free with MOPS buffer 50 mM+NaHCO$_3$ 8 mM (1/1)
SF56=Medium NaHCO$_3$-free with Sod-β 25 mM+NaHCO$_3$ 8 mM (1/1)

SF57=Medium NaHCO$_3$-free with TES buffer 40 mM+NaHCO$_3$ 8 mM (1/1)
SF58=Medium NaHCO$_3$-free with Trizma base buffer 50 mM+NaHCO$_3$ 8 mM (1/1)

C: Buffer screen for titre on days 8 and 11
SF01=Medium NaHCO$_3$-free with HEPES buffer 100 mM (1/2)
SF02=Medium NaHCO$_3$-free with HEPES buffer 100 mM (2/2)
SF03=Medium NaHCO$_3$-free with HEPES buffer 60 mM (1/2)
SF04=Medium NaHCO$_3$-free with HEPES buffer 60 mM (2/2)
SF05=Medium NaHCO$_3$-free with MOPS buffer 100 mM (1/2)
SF06=Medium NaHCO$_3$-free with MOPS buffer 100 mM (2/2)
SF07=Medium NaHCO$_3$-free with MOPS buffer 50 mM (1/2)
SF08=Medium NaHCO$_3$-free with MOPS buffer 50 mM (2/2)
SF09=Medium NaHCO$_3$-free with Sod-β 50 mM (1/2)
SF10=Medium NaHCO$_3$-free with Sod-β 50 mM (2/2)
SF11=Medium NaHCO$_3$-free with Sod-β 25 mM (1/2)
SF12=Medium NaHCO$_3$-free with Sod-β 25 mM (2/2)
SF13=Medium NaHCO$_3$-free with TES 80 mM (1/2)
SF14=Medium NaHCO$_3$-free with TES 80 mM (2/2)
SF15=Medium NaHCO$_3$-free with TES 40 mM (1/2)
SF16=Medium NaHCO$_3$-free with TES 40 mM (2/2)
SF17=Medium NaHCO$_3$-free with Trizma base 50 mM (1/2)
SF18=Medium NaHCO$_3$-free with Trizma base 50 mM (2/2)
SF19=Medium NaHCO$_3$-free with Trizma base 100 mM (1/2)
SF20=Medium NaHCO$_3$-free with Trizma base 100 mM (2/2)
SF21=Medium A (control) (1/2)
SF22=Medium A (control) (2/2)
SF23=Medium A Blank (=Medium A MOPS-free NaHCO$_3$-free) (1/2)
SF24=Medium A Blank (=Medium A MOPS-free NaHCO$_3$-free) (2/2)
SF49=Medium NaHCO$_3$-free with HEPES buffer 60 mM+NaHCO$_3$ 8 mM (1/1)
SF50=Medium NaHCO$_3$-free with MOPS buffer 50 mM+NaHCO$_3$ 8 mM (1/1)
SF51=Medium NaHCO$_3$-free with Sod-β 25 mM+NaHCO$_3$ 8 mM (1/1)
SF52=Medium NaHCO$_3$-free with TES buffer 40 mM+NaHCO$_3$ 8 mM (1/1)
SF53=Medium NaHCO$_3$-free with Trizma base buffer 50 mM+NaHCO$_3$ 8 mM (1/1)

Figure 3:
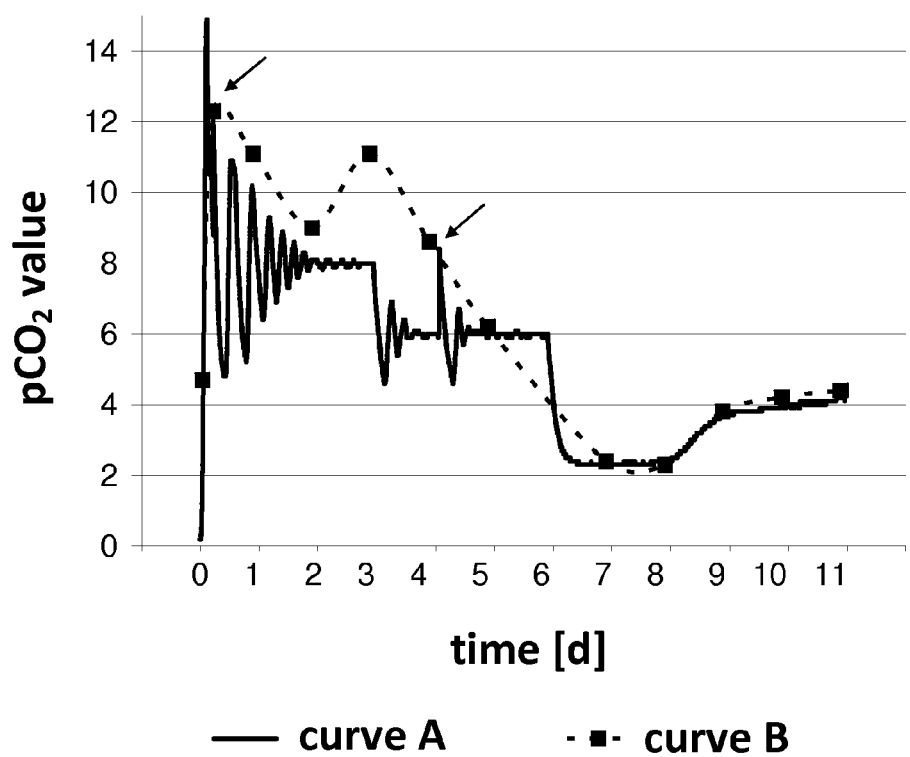

FIG. 3 pCO$_2$ REGULATION

FIG. 3 graphically shows the course of the internal pCO$_2$ measurement (probe with automatic data archiving) and of the external measured value on the blood gas analyzer (BGA) plotted over time. The first calibration marked with an arrow (comparison between CO$_2$ probe and BGA) on day 0 (d0) shows little effect as the regulating characteristics are still too unsettled. From the 2nd calibration (2nd arrow) on day 4 (d4) a good correspondence between the internal and external measured values can be detected. Axial representation: pCO$_2$-online vs pCO$_2$-BGA Curve A=CO$_2$ measurement internal (via CO$_2$ probe, Messrs Mettler Toledo)
Curve B=CO$_2$ measurement external (via BGA Rapidlap, Messrs Siemens)

FIG. 4 NORMAL LIVING CELL COUNT CONCENTRATION (A) OR TITRE CONCENTRATION (B)

A: Live cell count concentration (Cf. pCO$_2$-regulated/unregulated)
A=FS 33.1 Medium B NaHCO$_3^-$-free MOPS-free+40 mM TES (pCO$_2$-regulated) pH agent: NaOH
B=FS 32.2 Medium B NaHCO$_3$-free MOPS-free+40 mM TES+8 mM NaHCO$_3$ (unregulated) pH agent: NaOH
C=FS 32.3 Medium B, NaHCO$_3$-free, MOPS-free+40 mM TES+8 mM NaHCO$_3$ (unregulated) pH agent: Na$_2$CO$_3$ B: Standardised titre (cf. pCO$_2$-Regulated/Unregulated)
A=FS 33.1 Medium B, NaHCO$_3$-free, MOPS-free+40 mM TES (pCO$_2$-regulated) pH agent: NaOH
B=FS 32.2 Medium B, NaHCO$_3$-free, MOPS-free+40 mM TES+8 mM NaHCO$_3$ (unregulated) pH agent: NaOH
C=FS 32.3 Medium B, NaHCO$_3$-free, MOPS-free+40 mM TES+8 mM NaHCO$_3$ (unregulated) pH agent: Na$_2$CO$_3$

FIG. 5 COMPARISON BUFFER SYSTEMS

A: pCO$_2$ profile regulated/unregulated
A=FS 33.1 Medium B, NaHCO$_3$-free, MOPS-free+40 mM TES (pCO2-regulated) pH agent: NaOH
B=FS 32.2 Medium B, NaHCO$_3$-free, MOPS-free+40 mM TES+8 mM NaHCO$_3$ (unregulated) pH agent: NaOH
C=FS 32.3 Medium B, NaHCO$_3$-free, MOPS-free+40 mM TES+8 mM NaHCO$_3$ (unregulated) pH agent: Na$_2$CO$_3$ B: pCO$_2$ profile regulated (1×)/unregulated(5×)
I=FS 32.2 Medium B, NaHCO$_3$-free, MOPS-free+TES 40 mM+NaHCO$_3$ 8 mM (NaOH)
II=FS 33.1 Medium B, NaHCO$_3$-free, MOPS-free+TES 40 mM (pCO2-regulated) (NaOH)
III=FS 32.4 Medium B, NaHCO$_3$-free, MOPS-free+Sod-β 25 mM (NaOH)
IV=FS 32.5 Medium B, NaHCO$_3$-free, MOPS-free+Sod-β 25 mM+NaHCO$_3$ 12 mM (NaOH)
V=FS 33.3 Medium B, NaHCO$_3$-free, MOPS-free+NaHCO$_3$ 36 mM (comp. control) (NaOH)
VI=FS 33.5 Medium B, NaHCO$_3$-free, MOPS-free+NaHCO$_3$ 8 mM (NaOH)

C: Standardised titre
I=FS 32.2 Medium B, NaHCO$_3$-free, MOPS-free+TES 40 mM+NaHCO$_3$ 8 mM (NaOH)
II=FS 33.1 Medium B, NaHCO$_3$-free, MOPS-free+TES 40 mM (pCO2-regulated) (NaOH)
III=FS 32.4 Medium B, NaHCO$_3$-free, MOPS-free+Sod-β 25 mM (NaOH)
IV=FS 32.5 Medium B, NaHCO$_3$-free, MOPS-free+Sod-β 25 mM+NaHCO$_3$ 12 mM (NaOH)
V=FS 33.3 Medium B, NaHCO$_3$-free, MOPS-free+NaHCO$_3$ 36 mM (comp. control) (NaOH)
VI=FS 33.5 Medium B, NaHCO$_3$-free, MOPS-free+NaHCO$_3$ 8 mM (NaOH)

The product titres or product concentrations obtained with TES buffer are at the same level as those of the control.

FIG. 6 COMPARISON OF BUFFER SYSTEMS—STANDARDISED PRODUCT CONCENTRATION

Figure 6:
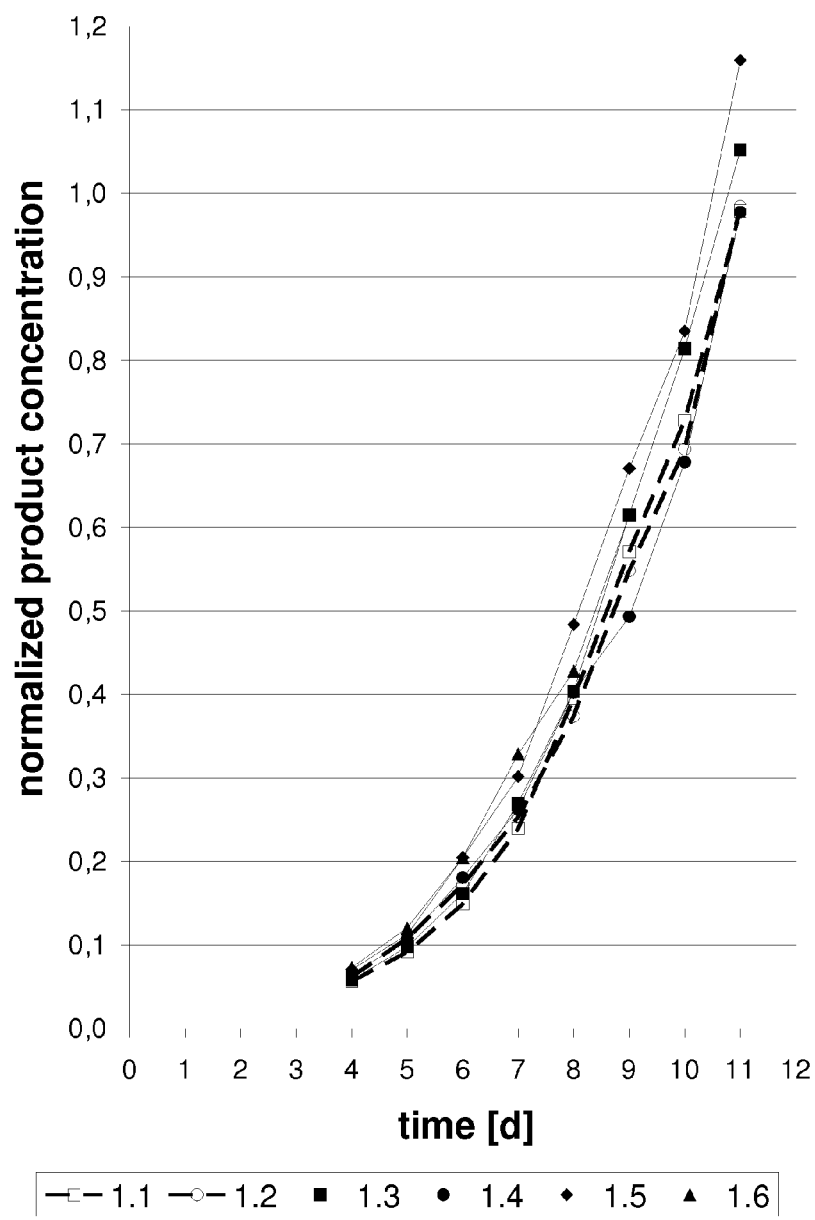

Runs 1.1 to 1.6 in FIG. 6 with CO$_2$ regulation and NaOH 1.2M as the alkaline solution.
1.1=FS 33.1 Medium B, NaHCO$_3$-free, MOPS-free+TES 40 mM
1.2=FS 33.2 Medium B, NaHCO$_3$-free, MOPS-free+TES 40 mM+NaHCO$_3$ 8 mM
1.3=FS 33.2 Medium B, NaHCO$_3$-free, MOPS-free+Sod-β 25 mM 1.4=FS 33.2 Medium B, $NaHCO_3$-free, MOPS-free+Sod-β 25 mM+$NaHCO_3$ 8 mM 1.5=FS 33.2 Medium B, $NaHCO_3$-free, MOPS-free+Sod-β 25 mM+$NaHCO_3$ 12 mM 1.6=FS 33.2 Medium B, $NaHCO_3$-free, MOPS-free+Sod-β 25 mM+$NaHCO_3$ 16 mM

FIG. 7 COMPARISON OF $CO_2$ PROFILES

Figure 7:
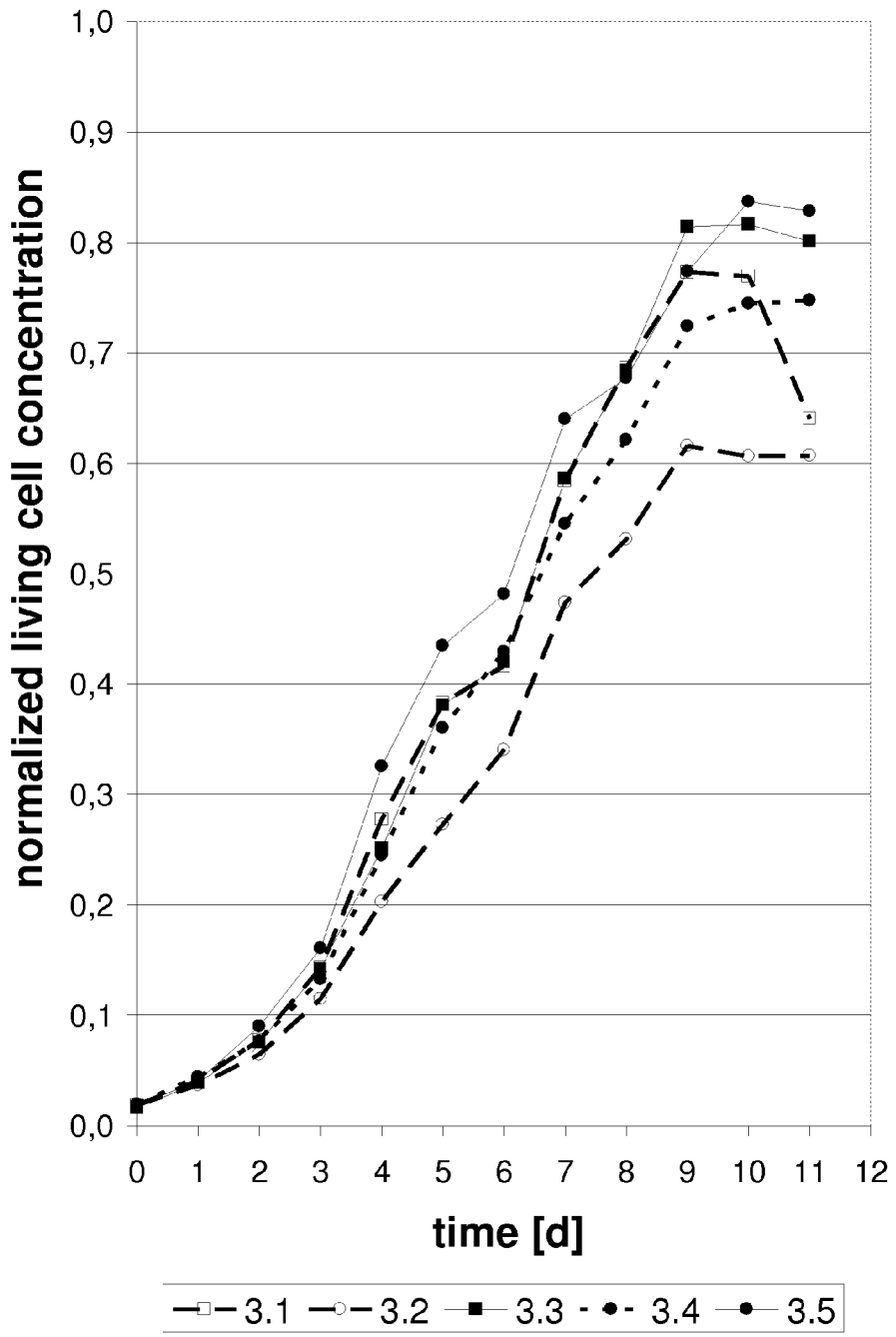
Figure 7:
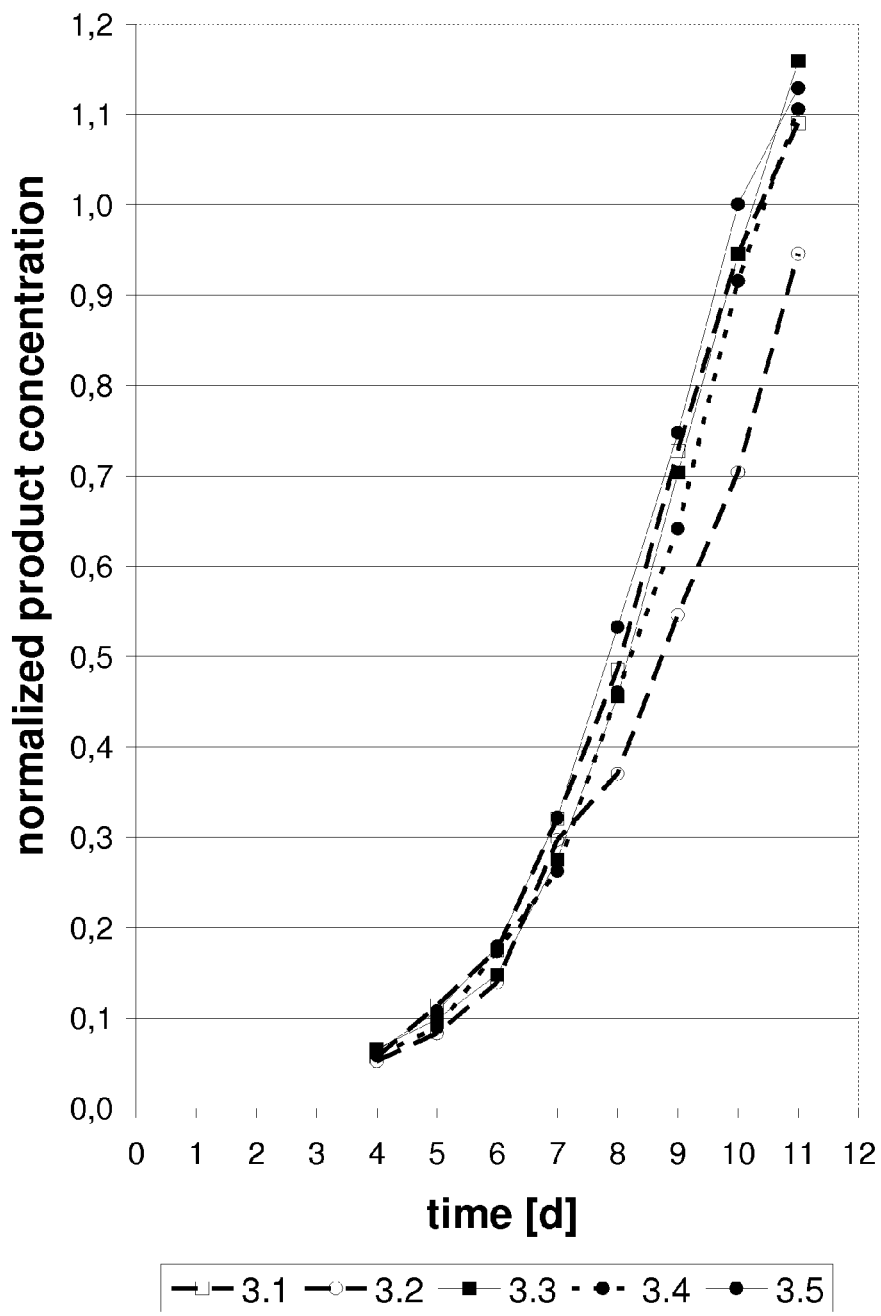

Runs 3.1 to 3.5 in FIG. 7 with $CO_2$ regulation, NaOH 1.2M as the alkaline solution and with Medium B, $NaHCO_3$-free, MOPS-free+Sod-β 25 mM Different $CO_2$ profiles:
  3.1=day 0-3 5% $CO_2$, day 3-11 3% $CO_2$
  3.2=day 0-2 8% $CO_2$, day 2-11 6% $CO_2$
  3.3=day 0-4 8% $CO_2$, day 4-8 10% $CO_2$, day 8-11 8% $CO_2$
  3.4=day 0-1 8% $CO_2$, day 1-2 6% $CO_2$, day 2-7 8% $CO_2$, day 7-11 5% $CO_2$
  3.5=day 0-11 3% $CO_2$

FIG. 8 ACID COMPATIBILITY WITH USE OF THE NA SALTS

SF1-10 with use of Medium B, $NaHCO_3$-free, MOPS-free+Sod-β 25 mM and addition of different Na salts on day 3:
  SF1=addition of water (for control)
  SF2=addition of water (for control)
  SF3=addition of sodium chloride (for hydrochloric acid)
  SF4=addition of sodium chloride (for hydrochloric acid)
  SF5=addition of sodium acetate (for acetic acid)
  SF6=addition of sodium acetate (for acetic acid)
  SF7=addition of sodium sulphate (for sulphuric acid)
  SF8=addition of sodium sulphate (for sulphuric acid)
  SF9=addition of disodium hydrogen phosphate (for phosphoric acid)
  SF10=addition of disodium hydrogen phosphate (for phosphoric acid)

FIG. 9 COMPARISON OF DIFFERENT ACIDS

Figure 9:
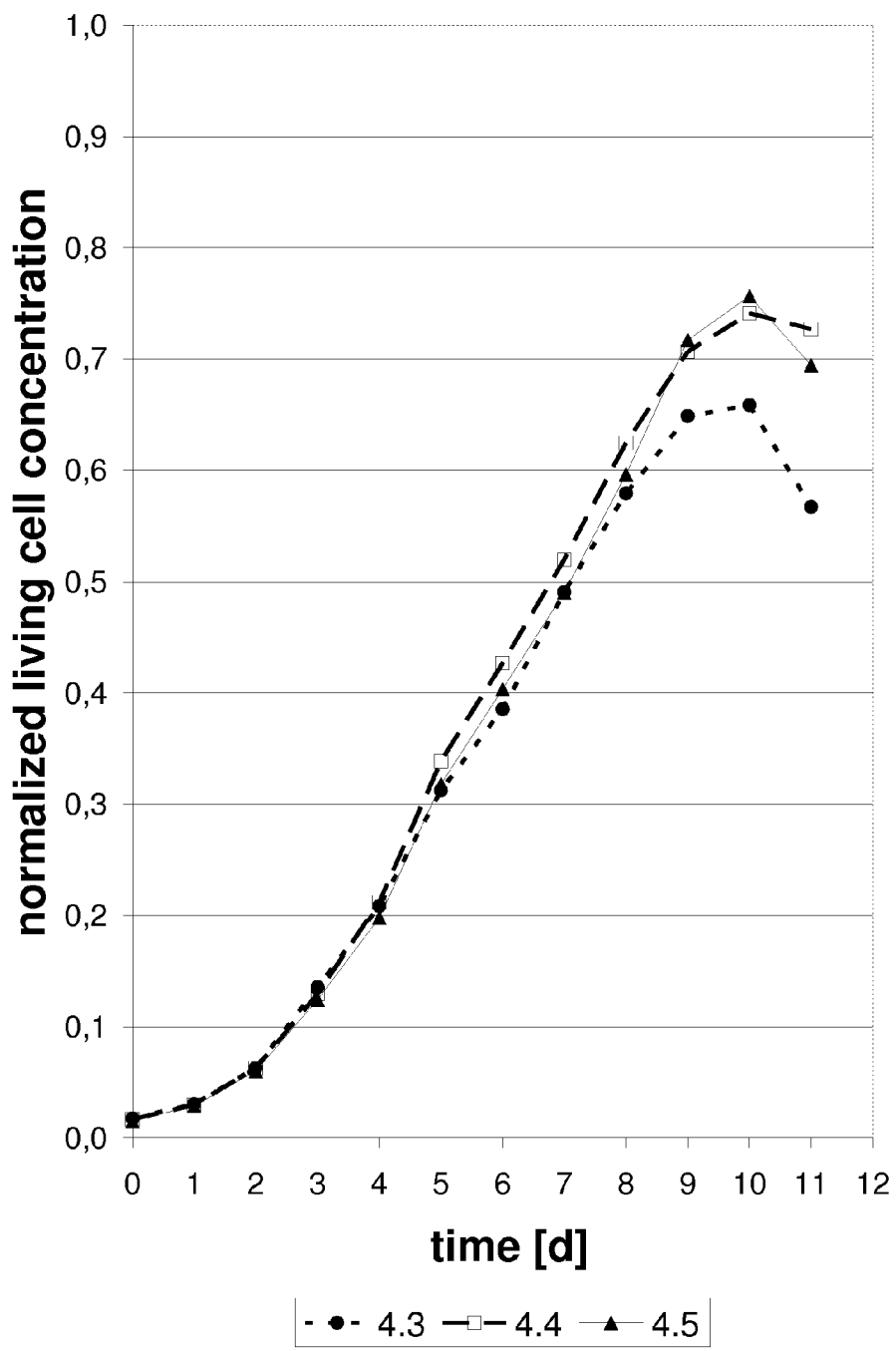
Figure 9:
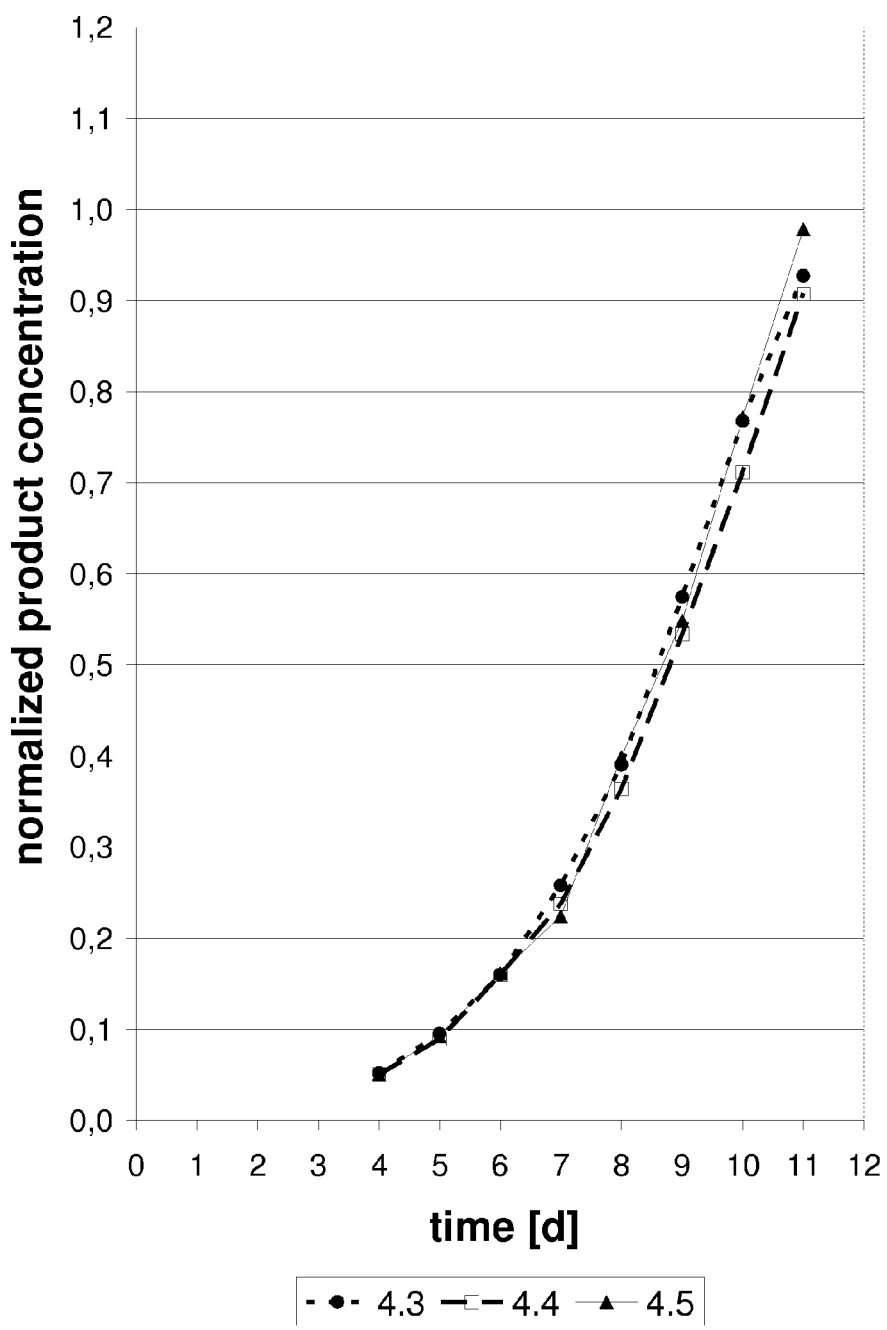
Figure 9:
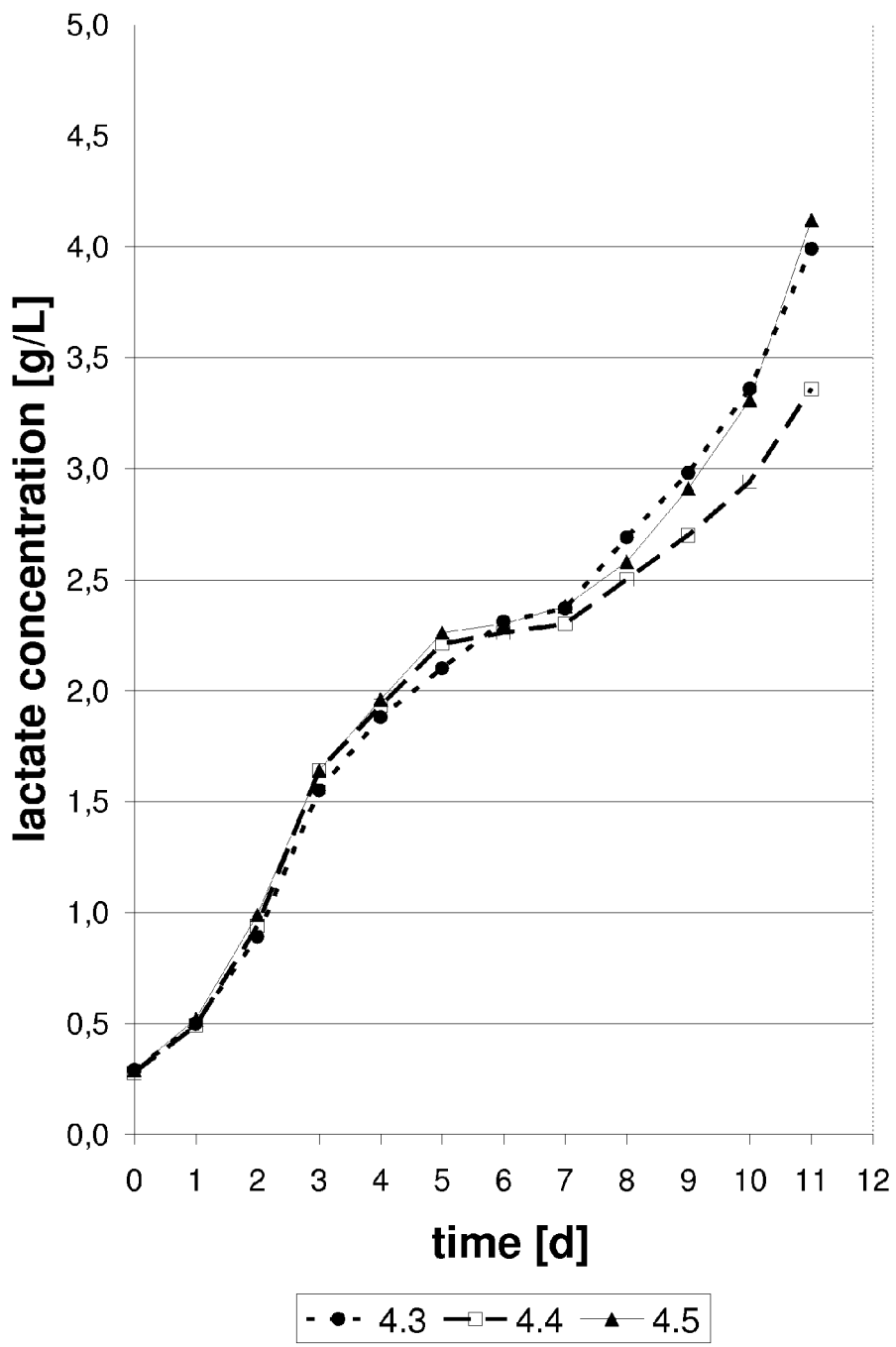
Figure 10:
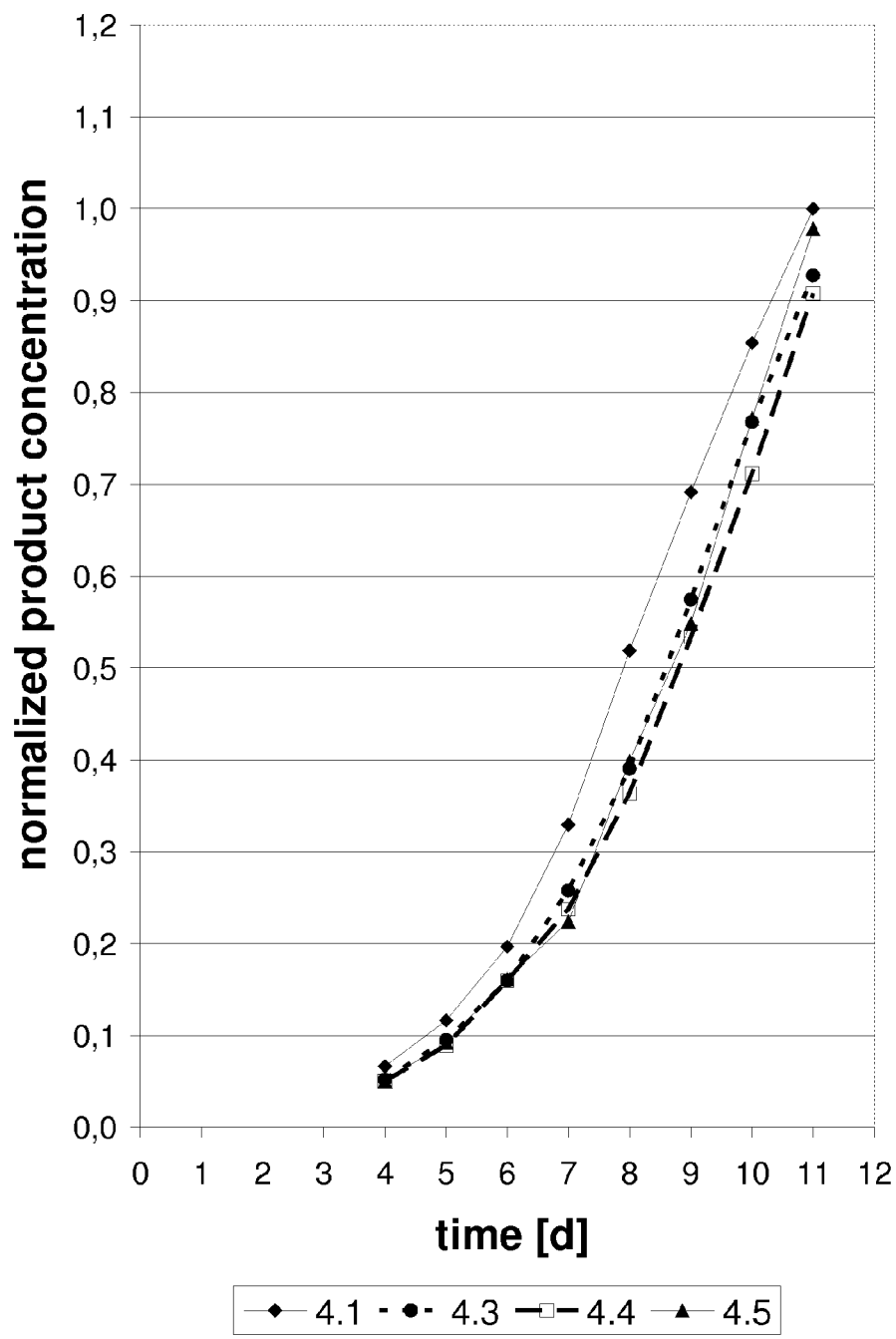

Runs 4.3 to 4.5 in FIG. 9 with $CO_2$ regulation, NaOH 1.2M as the alkaline solution, with Medium B, $NaHCO_3$-free, MOPS-free+Sod-β 25 mM and addition of different acids (50 ml) on day 3:
  4.3=addition of hydrochloric acid 99 mM
  4.4=addition of phosphoric acid 81 mM
  4.5=addition of sulphuric acid 54 mM FIG. 10 COMPARISON OF STANDARD PROCESS WITHOUT $CO_2$ REGULATION WITH $CO_2$—REGULATED PROCESS 4.1=Medium B, $Na_2CO_3$ 1M as the alkaline solution, without $CO_2$ regulation (standard process)

4.3=Medium B, $NaHCO_3$-free, MOPS-free+Sod-β 25 mM, NaOH 1.2M as the alkaline solution, with $CO_2$ regulation and addition of hydrochloric acid 99 mM 4.4=Medium B, $NaHCO_3$-free, MOPS-free+Sod-β 25 mM, NaOH 1.2M as the alkaline solution, with $CO_2$ regulation and addition of phosphoric acid 81 mM 4.5=Medium B, $NaHCO_3$-free, MOPS-free+Sod-β 25 mM, NaOH 1.2M as the alkaline solution, with $CO_2$ regulation and addition of sulphuric acid 54 mM

FIG. 11 COMPARISON OF $CO_2$—PROFILES WITH MODEL CELL 2

Figure 11:
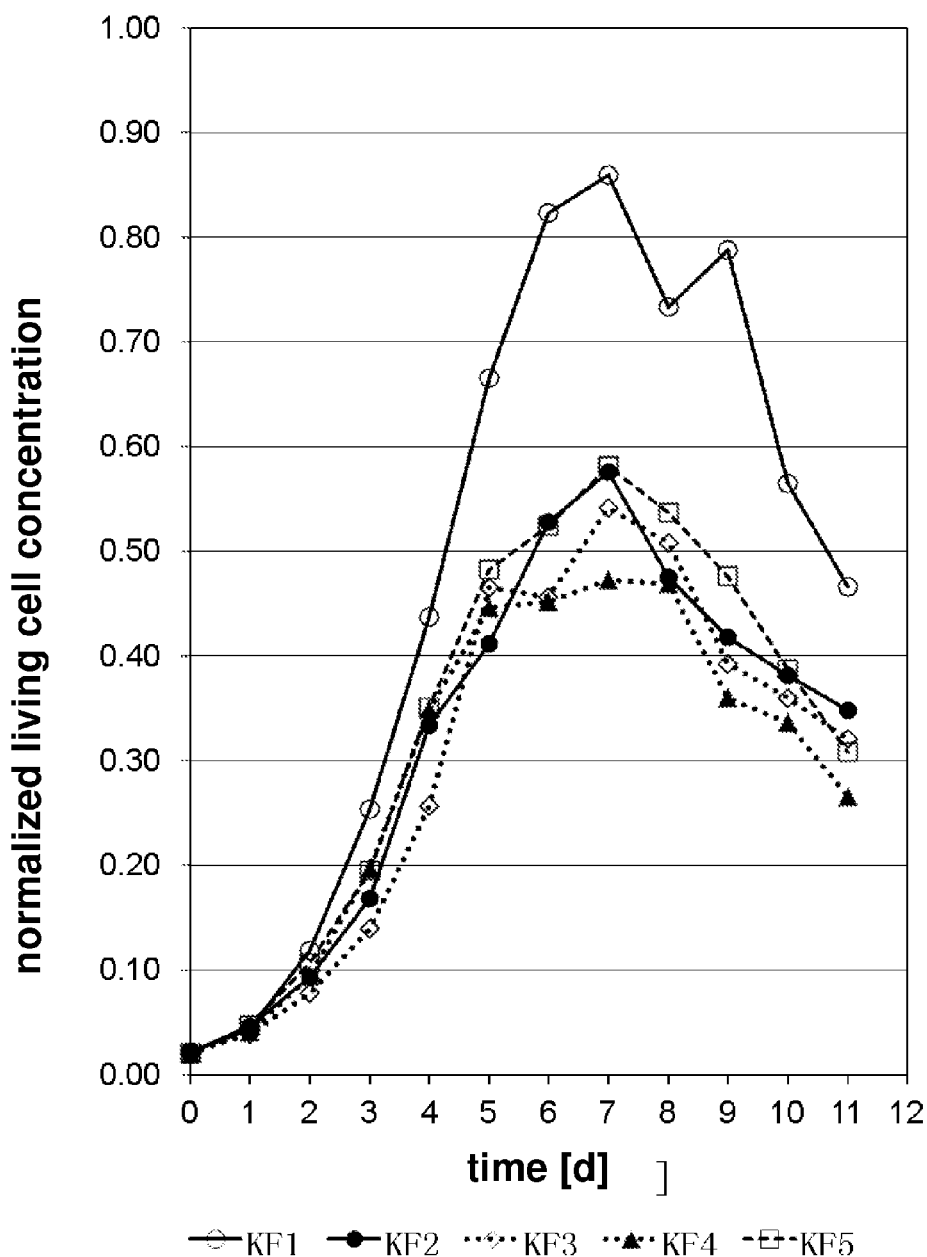
Figure 11:
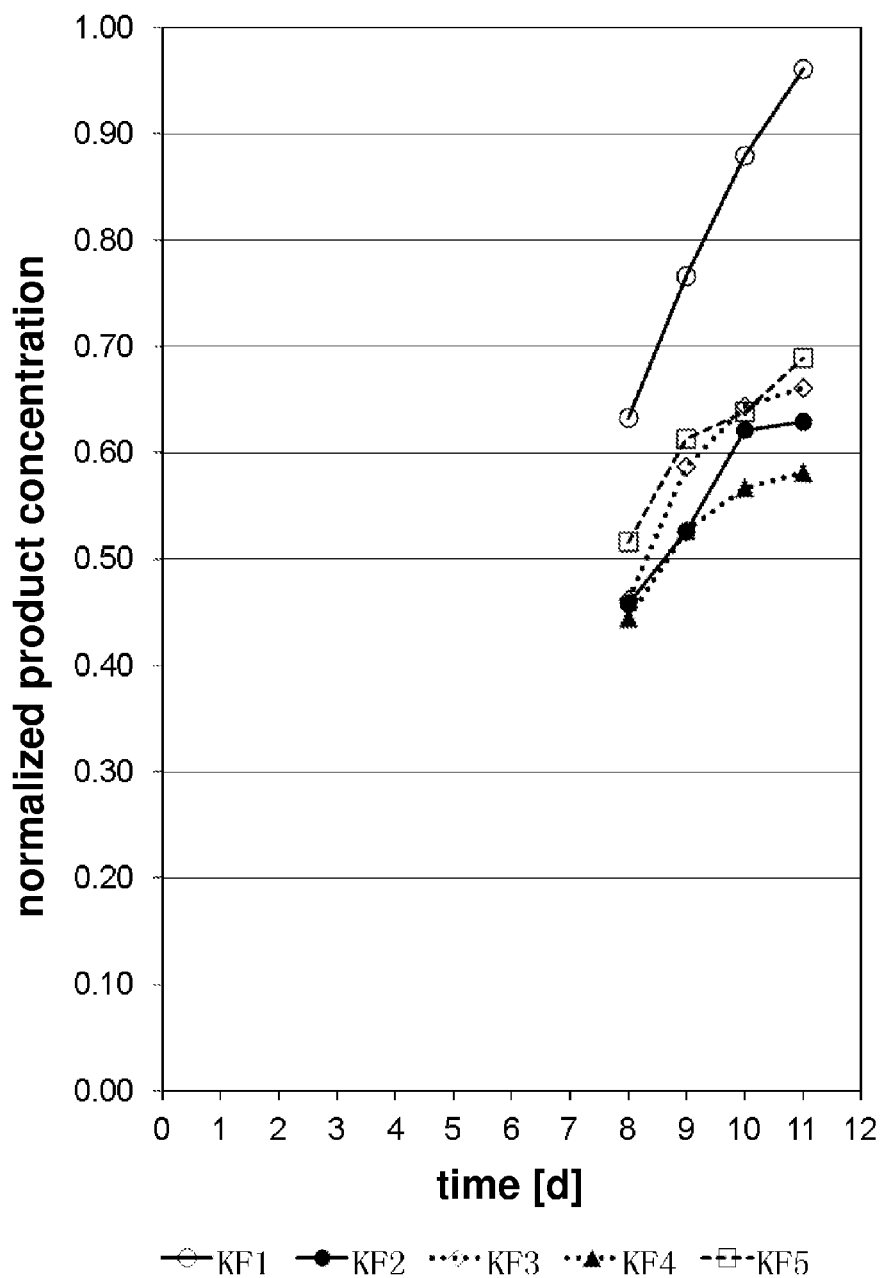
Figure 11:
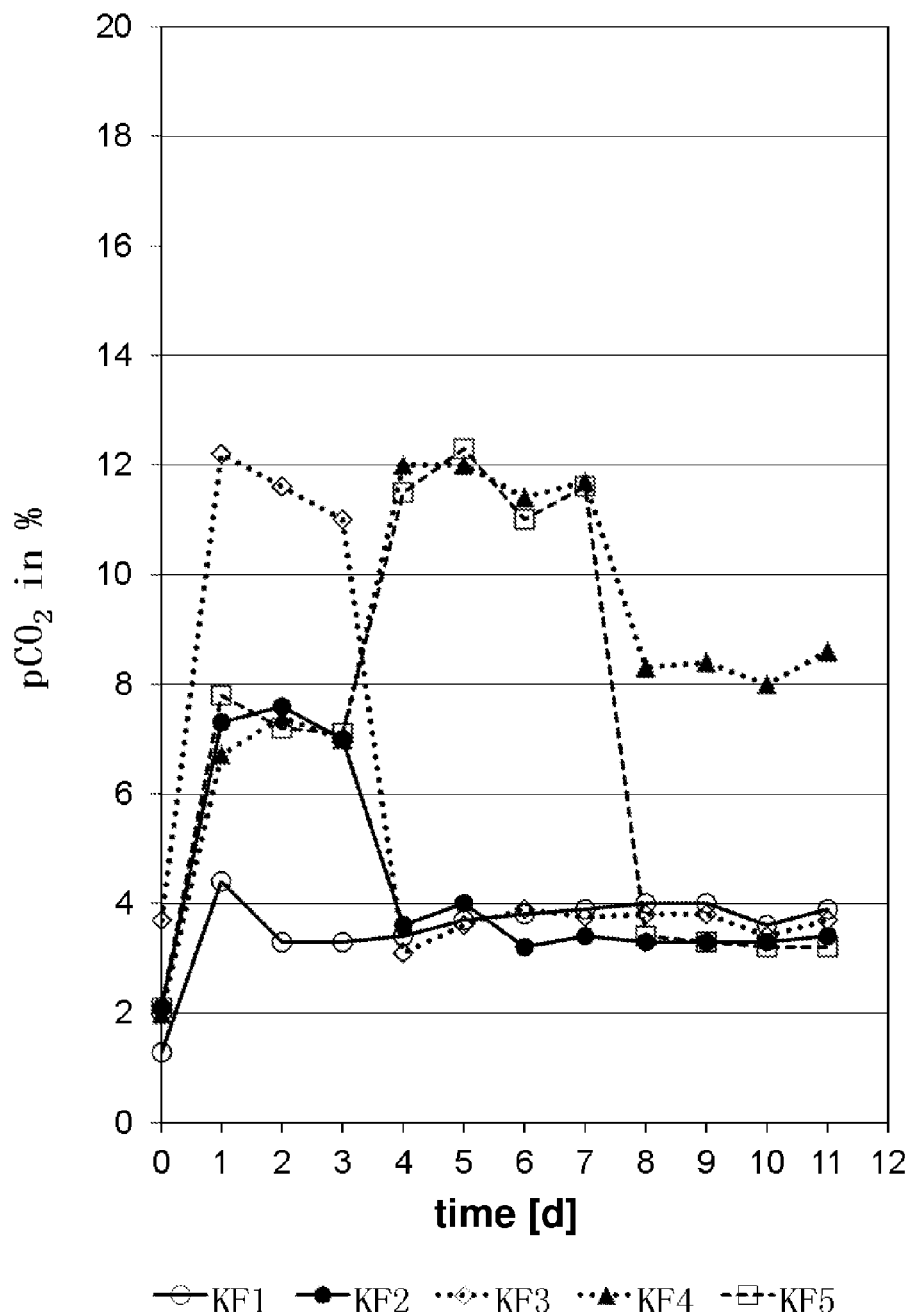

(A) Standardised cell concentration, (B) standardised product concentration, (C) $CO_2$ profiles Runs KF1 to KF5 in FIG. 11 with $CO_2$ regulation, NaOH 1.2M as the alkaline solution and with Medium B, $NaHCO_3$-free, MOPS-free+Sod-β 25 mM Different $CO_2$ profiles:
  KF1=day 0-11 3% $CO_2$
  KF2=day 0-3 7% $CO_2$, day 3-11 3% $CO_2$
  KF3=day 0-3 11% $CO_2$, day 3-11 3% $CO_2$
  KF4=day 0-3 7% $CO_2$, day 3-7 11% $CO_2$, day 7-11 7% $CO_2$
  KF5=day 0-3 7% $CO_2$, day 3-7 11% $CO_2$, day 7-11 3% $CO_2$

DETAILED DESCRIPTION OF THE INVENTION

The experiments show, by way of example:

Result 1:
  The reduced NaHCO3 concentration of 12 mmol/L and particularly of 8 mmol/L indicates an advantageous $pO_2$ profile (cell growth) similar to that of the control.

Result 2:
  Identification of the best buffer substances in $NaHCO_3$ free cell culture medium or in $NaHCO_3$ lowered (=8 mmol/L) cell culture medium.
  The best buffer substances are: TES (e.g. 40 mmol/L) and Sod-β (e.g. 25 mmol/L)

Figure 2A:
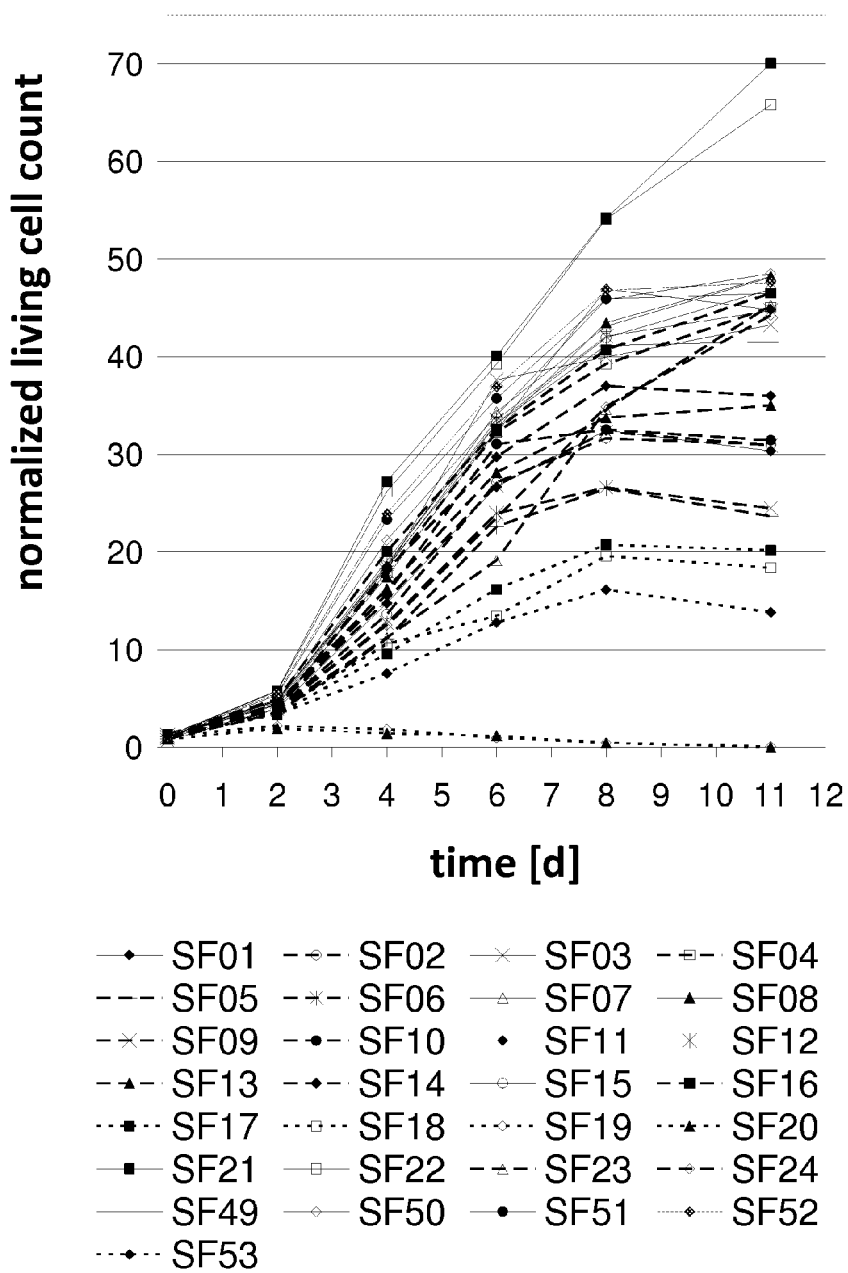

FIG. 2A shows that all the buffer medium mixtures, except for Trizma base (SF19 and SF20) of concentration I exhibit cell growth. The best growth is found in the two controls (SF21 and SF22), but the difference from the buffer medium mixtures is relatively small, at least up to d8. The three best buffers, with a cell density in the region of 45, are Sod-β/H; TES/K+$NaHCO_3$/D and MOPS/F+$NaHCO_3$/D. Trizma base runs poorly in every concentration; the pH is certainly stable but there may be some toxicity present.

Figure 2B:
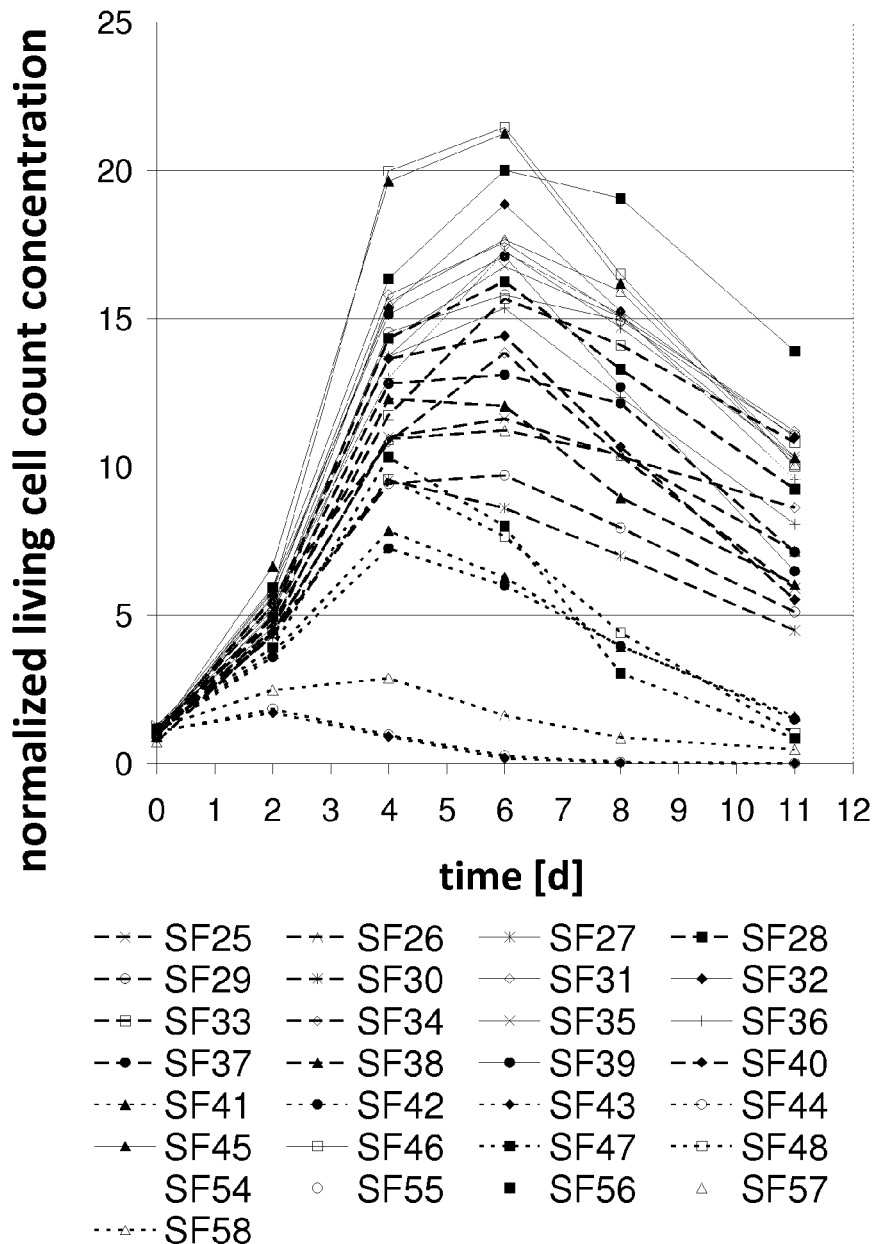

In FIG. 2B the same scale has been used as in FIG. 2A. It is clearly apparent that the cell densities achieved in this $CO_2$ profile turn out to be substantially lower. The controls certainly come out on top here too, but a maximum cell density of 20 is unacceptable. The two best buffer mixtures here, with a cell density in the region of 18, are Sod-β/H+ $NaHCO_3$/D and MOPS/F. For this reason, the further evaluation is restricted primarily to the shake flasks from incubator 1 with the associated $CO_2$ profile.

Figure 2C:
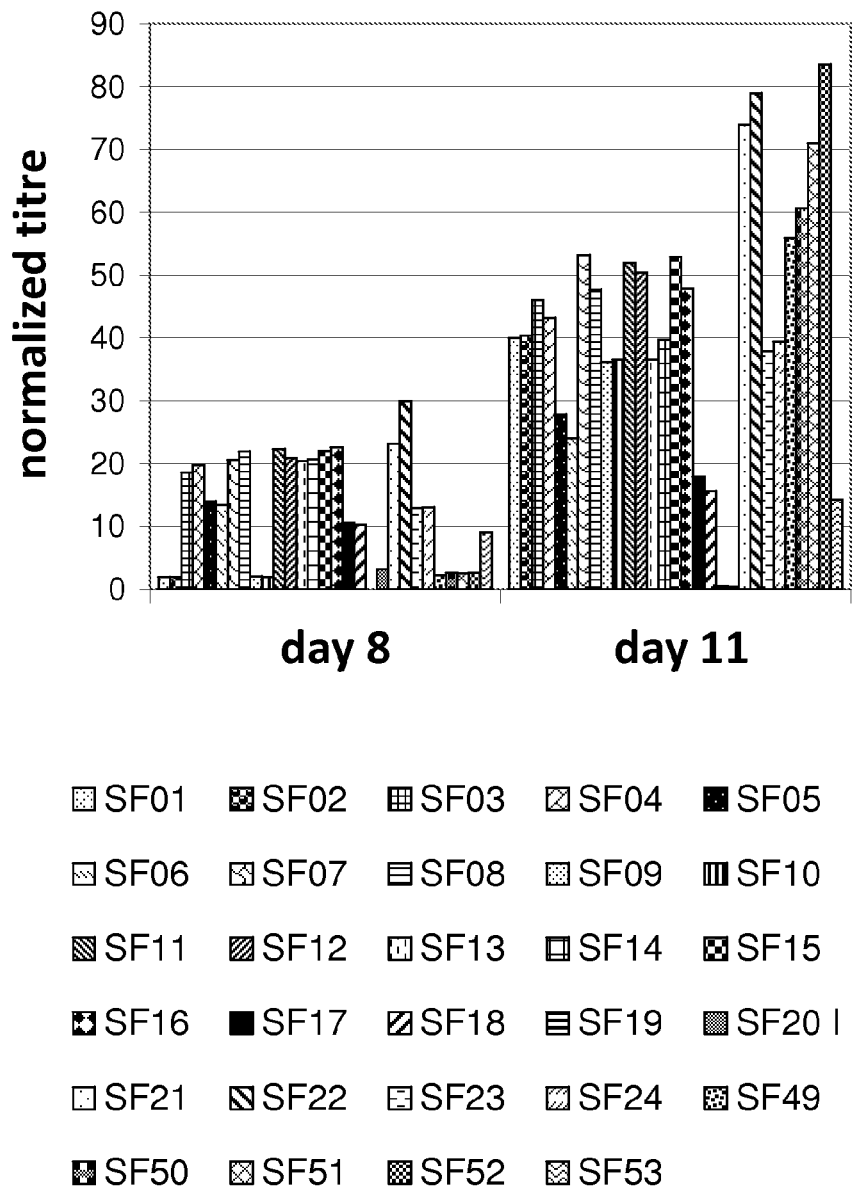

Generally, the combination with $NaHCO_3$/D is advantageous at the low buffer concentrations. FIG. 2C shows the titre concentrations obtained (standardised). With a few exceptions, an increasing titre can be seen between d8 and d11. The gain is thus even more than tenfold in the shake flasks SF49 to SF52, the media with the reduced $NaHCO_3$ concentration!

Another remarkable fact is that for the first time the conventional control (SF21 and SF22) has been overtaken with a new buffer substance in the medium: SF52 with TES/K+$NaHCO_3$/D give very good results on d11 with a standardised product concentration of 83.6.

Result 3
  The $pCO_2$ regulating experiments show that with a desired $pCO_2$ value of 2% a critical lower limit is reached which does not appear sensible in the process.

Figure 4B:
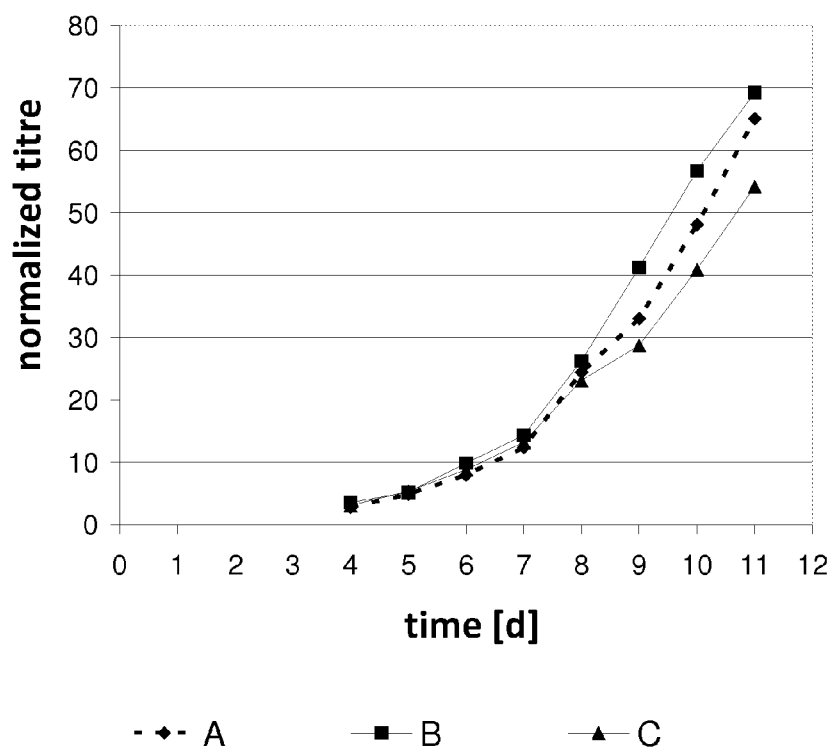

Result 4:
  FIGS. 4 A and B, relating to the normal live cell count concentration (A) and titre concentration (B), respectively, show that the cell-specific product formation rate of the regulated fermentation run (curve with triangular symbol) is higher than that of the comparable unregulated fermentation run (curve with diamond). In addition, the tests in FIG. 4 show that pH regulation with NaOH tends to have a better product formation rate than that using $Na_2CO_3$. When the $pCO_2$ profile is further optimised the specific product formation rate is increased still more. The live cell count density of the $pCO_2$-regulated run (FS 33.1) deviates from one another by a maximum of 20 units, as can be seen in FIG. 4B. From d10 the two comparison runs also show very little divergence, otherwise a good conformity is obtained. The lower level of FS 33.1 can result from the higher pCO$_2$ profile and cannot be interpreted negatively. The vitality (not shown) is at the same level in all the runs. The consumption of alkaline solution (not shown) is low in every run. At FS 32.2 (highest live cell count concentration) more alkaline solution has to be added towards the end of fermentation (d9-d11), as expected. However, this run has the lowest osmolality (not shown) at the end of fermentation, at 393 mosmol/kg. FIG. 4A shows that FS 33.1 has a higher titre concentration, in spite of having a lower cell count than FS 32.3. The concentration is in the upper third of the scatter between the two identical fermentation runs FS 32.2 and FS 32.3. This means that the fermentation run with the pCO$_2$ regulation has a higher specific production formation rate.

Result 5:

Ideally a fermentation run takes place under the following conditions: TES buffer (or Sod-β buffer) completely without NaHCO$_3$ and with pCO$_2$ regulation. The best end titres are achieved in this way.

Figure 5:
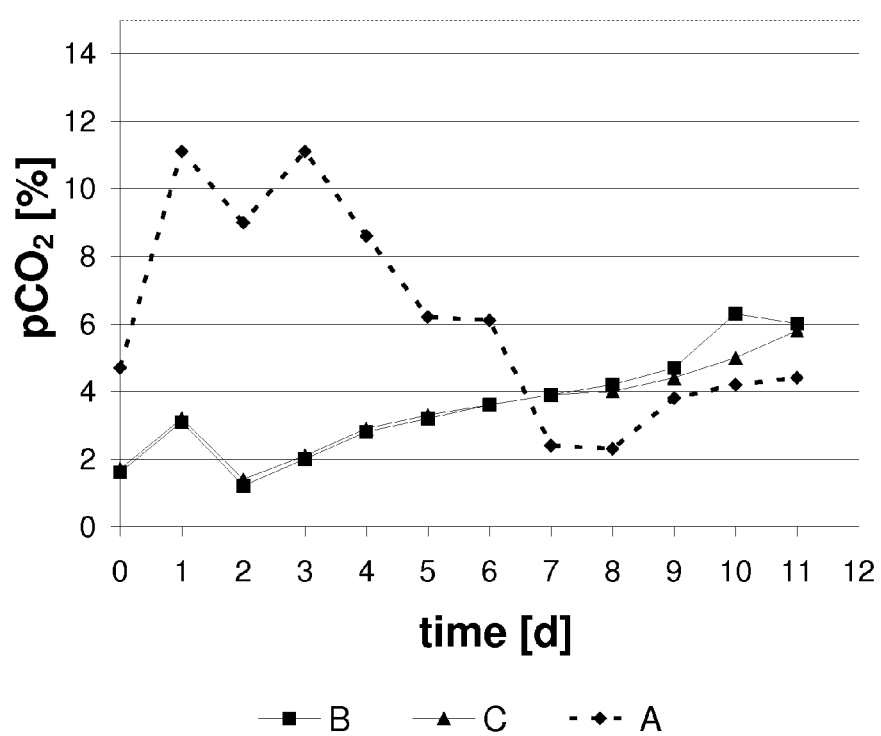
Figure 5:
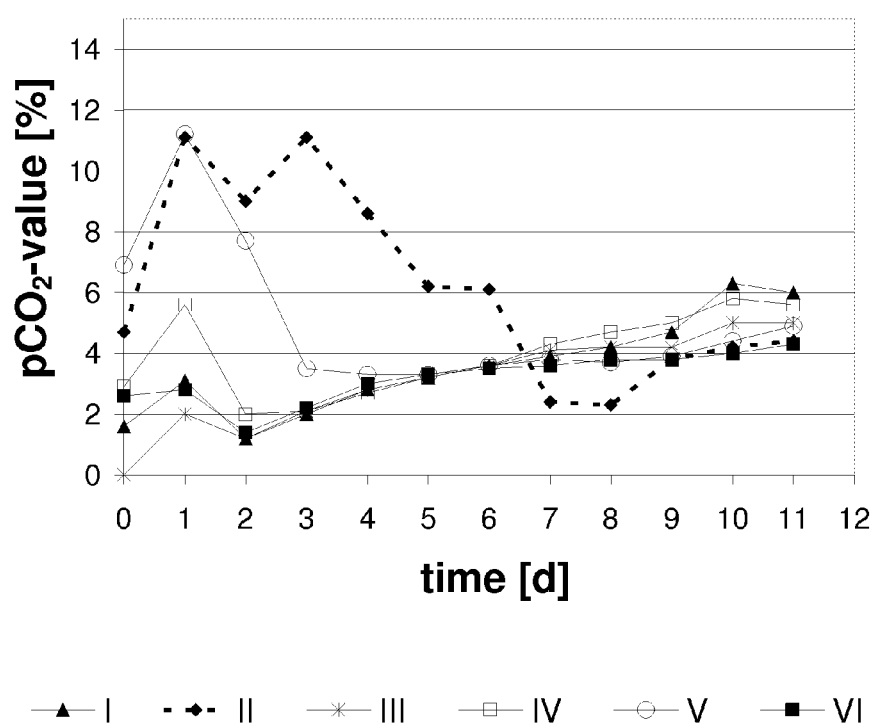
Figure 5:
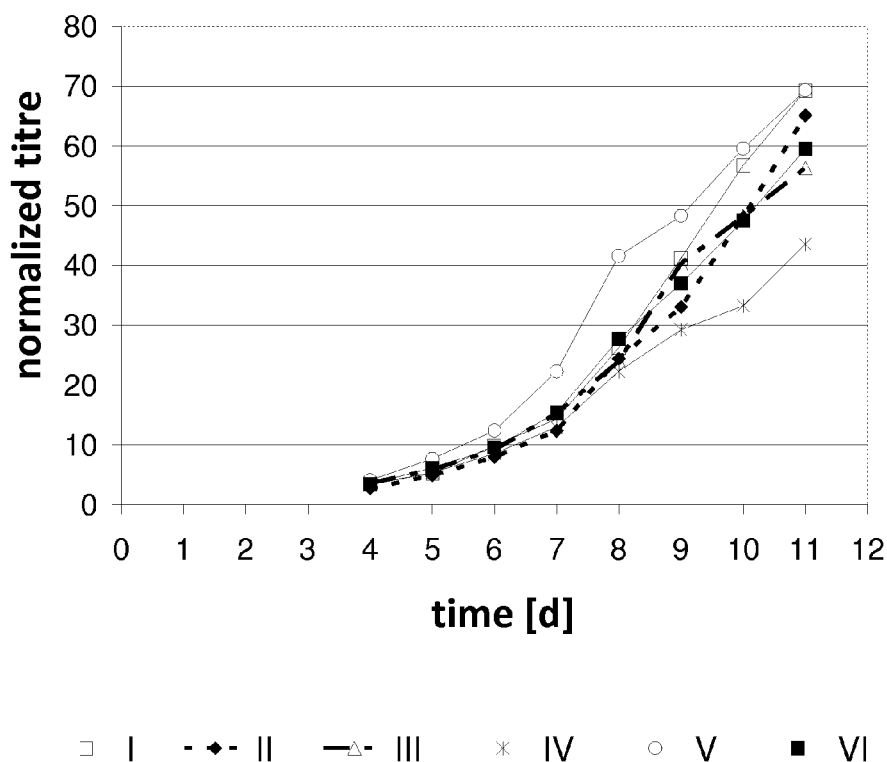

FIG. 5A shows that the pCO$_2$ profile of the regulated fermentation run (FS33.1) is clearly distinguished from the comparison fermentations (FS32.2 and FS32.3). FS32.2 and FS32.3 are used for the comparison, although they have a smaller amount of NaHCO3, as an identical comparison partner has been eliminated owing to contamination. The pCO$_2$ profile obtained by regulation is clearly distinguished from the comparison runs in the first third of the fermentation and largely follows the prescribed values (cf. FIG. 5B, d1-d3 pCO$_2$=8%, d3-d6 pCO$_2$=6%, d6-d8 pCO$_2$=2% and from d8-d11 pCO$_2$=4%). When a lower than normal pCO$_2$ value is imposed (day 6-8, d6-d8) nitrogen gas is fed in so as to expel CO$_2$. It is found that the low desired value is never reached and a pCO$_2$ value of 3.2% represents a critical lower limit for the regulation. With the increased demands of nitrogen, oxygen is also expelled as a result, and this is compensated by a higher volume flow of oxygen. A critical total amount of gas can be achieved, in which an unreasonably large amount of foaming can be observed.

FIG. 5B shows that the regulated fermentation run is also surprisingly clearly distinguished from all the other comparison runs. This means that the pCO$_2$ profile achieved by regulation is actually based on the prescribed value (d1-d3 pCO$_2$=8%, d3-d6 pCO$_2$=6%, d6-d8 μCO$_2$=2% and from d8-d11 pCO$_2$=4%) and does not occur by accident.

FIG. 5C shows that the titre concentrations that are obtained with TES without NaHCO$_3$ or TES with 8 mmol/L NaHCO$_3$ are comparable with the control (NaHCO$_3$ based buffer with a concentration of 36 mmol/L). In spite of a randomly selected and non-optimised pCO$_2$ profile, the run with TES without NaHCO$_3$ (regulated) achieves a final concentration (titre) which differs from the control by only 6.10% (measured on the control). The run with TES plus 8 mmol/L NaHCO$_3$ (unregulated) achieves a final concentration (titre) which differs from the control by only 0.01% (measured on the control). This shows, totally surprisingly, that NaHCO$_3$ can be entirely replaced by TES. Moreover, it shows that the result of the run with TES plus 8 mmol/L NaHCO$_3$ (unregulated) achieves the same final titre concentration as the control.

Result 6:

To achieve the highest possible product concentration, it is surprisingly not necessary to use NaHCO$_3$ in the medium. The product concentrations of both runs, shown in FIG. 6, using TES (1.1, 1.2) astonishingly have the same product concentrations both with and without the use of NaHCO$_3$ in the medium. In the runs using Sod-β the product concentrations achieved are again not dependent on the amount of NaHCO$_3$ in the medium, as a similar maximum product concentration is achieved on day 11 in all the runs (1.3-1.6) (cf. FIG. 6). In the CO$_2$-regulated fermentation process it is, surprisingly, not necessary to use NaHCO$_3$ in the medium. With no NaHCO$_3$ in the medium the CO$_2$ regulation in the process is made easier as the medium cannot form any CO$_2$.

Result 7:

Surprisingly, it has been shown that a low CO$_2$ partial pressure at the start of the fermentation is a critical factor for an optimised fermentation result.

On the other hand, it is not advantageous to start a fermentation process with a high pCO$_2$. Both the live cell concentrations and also the product concentrations of all the runs apart from run 3.2 with different pCO$_2$ profiles proceed similarly and reach roughly the same maxima (cf. FIGS. 7A and 7B). In run 3.2 the cells grow less well and therefore achieve a lower product concentration.

Looking at the associated pCO$_2$ values in FIG. 7C a considerable difference can be seen between run 3.2 and all the other runs. The pCO$_2$ on day 1 in 3.2 is above 8%. On the other hand, the pCO$_2$ values of the other runs on day 1 are all below 5%.

The cell growth is inhibited by an initially high pCO$_2$.

Figure 8:
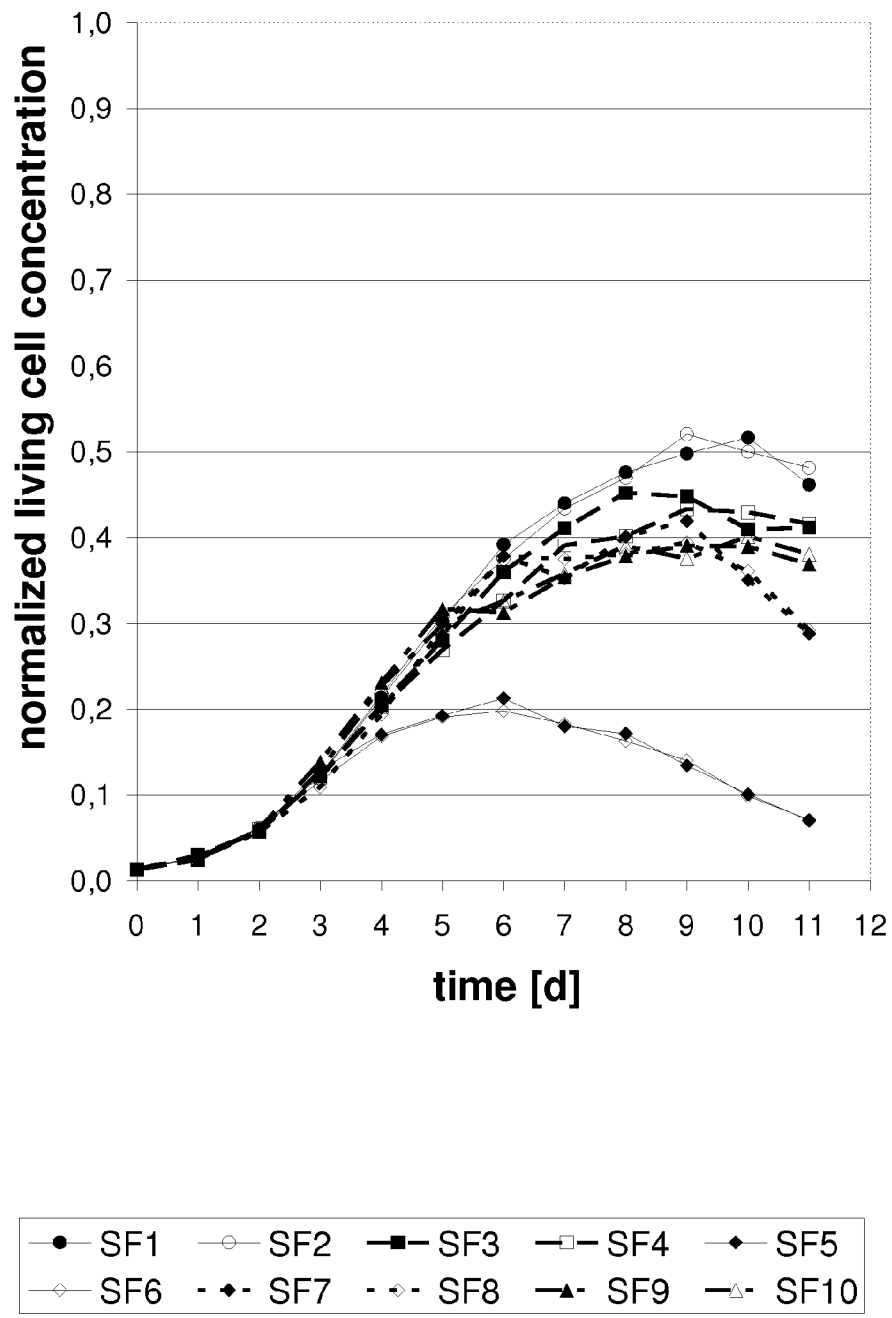

Result 8:

The live cell concentrations shown in FIG. 8 show that the cell growth is affected by the addition of sodium acetate (SF5 and 6). The live cell counts increase only slightly when sodium acetate is used and fall back again three days after the addition, so that it can be assumed that the sodium acetate has a toxic effect. Because of the cell toxicity demonstrated, acetic acid is not used as a preferred acid for pH regulation in the fermentation process. None of the other salts show any toxic effects on cell growth and can be used for testing in the fermentation process. Hydrochloric acid, sulphuric acid and phosphoric acid are preferred.

Result 9:

As a result of the addition of hydrochloric acid (4.3), sulphuric acid (4.4) and phosphoric acid (4.5) the same product concentrations are achieved in the fermentation process, as shown in FIG. 9B.

When the live cell concentrations of these mixtures are considered (cf. FIG. 9A) it is apparent that in run 4.3 with the addition of hydrochloric acid a lower cell count is obtained than in the other runs. However, as the product concentration is just as high as in all the other runs, the productivity of the cells is higher as a result of the addition of the hydrochloric acid. In run 4.4 with the addition of sulphuric acid, from day 7 onwards less lactate is formed than in the other runs, as shown in FIG. 9C. As lactate has a toxic effect on the cells upwards of a certain concentration, a low lactate concentration in the process is advantageous. Both sulphuric acid and hydrochloric acid are advantageous in the fermentation process. Sulphuric acid ensures a low lactate production and hydrochloric acid ensures high cell productivity.

Result 10:

When the standard process (4.1) is compared with the CO$_2$-regulated processes using different acids (4.3-4.5) similar product concentrations are obtained in all the runs (cf. FIG. 10). In run 4.5 with the addition of phosphoric acid approximately the same maximum product concentration is obtained as in run 4.1 (standard process).

The CO$_2$.regulated process does not involve any disadvantages in relation to the product concentration, compared with the standard process. When the CO$_2$-regulated process is further optimised, the product concentration can even be increased by comparison with the standard process.

To summarise, the results show a comparable performance in terms of cell growth and productivity and even an improved performance as a result of lower lactate formation when the acids tested are used to regulate pH.

Result 11:

In order to place the results of the process performance for different $pCO_2$ profiles, as described in Result 7, on a broader database, in Example 9 another test approach is used with different $pCO_2$ profiles, this time with a different model cell (CHO).

The different $pCO_2$ profiles that are used in this test approach are shown in FIG. 11C.

As is apparent from FIGS. 11A and 11B, the fermentation run KF1 both for the cell growth and for the pattern of the product concentration is clearly distinguished from the remaining set of curves. This fermenter run (KF1) was operated with a $pCO_2$ profile from day 0 to day 11 with 3% $pCO_2$.

This test approach was thus able to confirm that the partial $CO_2$ pressure at the start of fermentation (initial growth phase, particularly day 0 to 3) is an important factor for an optimised fermentation result.

Example 9 confirms that a deliberately selected low partial $CO_2$ pressure at the start of the fermentation yields the best results both for cell growth and for the pattern of the product concentration. This is also, or especially, true when using cultivation media with reduced $HCO_3^-$ or $CO_3^{2-}$ ions (particularly less than 12 mmol/L or 8 mmol/L of $HCO_3^-$ or $CO_3^{2-}$ ions) or when using cultivation media that are completely free from $HCO_3^-$ or $CO_3^{2-}$ ions.

DEFINITIONS

Before the more detailed description of the invention by means of the non-restrictive exemplifying embodiments that follow, it should be pointed out that the use of the indefinite article, for example "a" or "an" and the definite article, namely "the", includes both the singular and plural of the term in question, unless one of the two forms is explicitly ruled out and reference is made to a particular form (singular or plural). Thus, the term "a cell" automatically includes "a plurality of cells" as well, unless it is explicitly stated that only a single cell is meant. The singular is explicitly meant, for example, where "a" or "one" is supplemented by (1).

By a "biopharmaceutical production process" is meant the production of biomolecules by means of eukaryotic cells in a fermentation process. This includes in particular the production of proteins such as antibodies in mammalian cells such as CHO, NS0, PERC.6 cells.

By a biomolecule is meant in particular a protein of interest or a DNA or RNA molecule such as for example RNAi, anti-sense RNA etc.

The optimisation of a biopharmaceutical production process means the adaptation of the media and physical parameters in the fermentation process. These include for example $pCO_2$, the speed of the stirrers, etc. The optimisation improves for example the increase in the titre or the product quality (e.g. different glycosylation pattern of the protein or other posttranslational modifications of a protein) or the robustness of the process (lack of sensitivity to small process fluctuations, minor changes having no effect on the process).

The term "non-$CO_2$-forming acid and/or alkaline solution" refers to acids and alkaline solutions that do not give off $CO_2$ by a chemical reaction, such as for example NaOH, HCl, $H_3PO_4$, $CH_3COOH$, $H_2SO_4$.

"Regulation of the $pCO_2$" means that the partial $CO_2$ pressure in the fermentation solution is held at/adjusted to a desired value. This is done for example by supplying $CO_2$, $O_2$, $N_2$ and/or air during the bioprocess. In the present invention the "regulation of the $pCO_2$" is preferably done by supplying $CO_2$ and/or $N_2$ gas.

"Completely free from $HCO_3^-$ or $CO_3^{2-}$ ions" means that the medium used from day 0 to the end of the fermentation is free from $HCO_3^-$ or $CO_3^{2-}$ ions. No $HCO_3^-$ or $CO_3^{2-}$ ions are supplied to the medium through separate additions ("feeds") either, from day 0 to the end of the fermentation.

By a "fed-batch" fermentation/a "fed-batch" method or a "fed-batch" process is meant a fermentation process which is operated by an influx of substrates up to the maximum fill level. The term fed-batch is derived from the English word "fed" and batch, meaning stack or supply. Sometimes the term inflow process is used instead of the term fed-batch method. The term fed-batch fermentation/fed-batch method or fed-batch process is well established in process technology. These terms refer to processes that are run as a "stack", i.e. one after the other, and are operated by an influx (feed) of reagents (starting materials) up to the maximum fill level.

Within the scope of the present invention, fed-batch fermentation/the fed-batch method or the fed-batch process is preferably subdivided into three (3) sections: initial growth phase, growth phase, dying-off phase. The duration of a fed-batch fermentation is time-limited. Preferably, the entire duration of the fed-batch fermentation/fed-batch method or fed-batch process is 8-15 days, particularly preferably 11 days.

The fed-batch fermentation/the fed-batch method or the fed-batch process differs from other cultivation processes such as perfusion culture or fermentation in the perfusion process or continuous cultivation. In perfusion culture, the incubation reactor containing the cell culture is constantly rinsed with a flow of medium. This ensures constant concentration ratios of the nutrients, growth factors, antibiotics etc., the removal of metabolic end products and the simulation of natural physiological and metabolic ambient conditions (blood circulation, diffusion and circulation of tissue fluid).

The "specific productivity" or "specific product formation rate" of a cell indicates the quantity of a particular protein that is produced by a cell per unit of time, i.e. that is released into the medium, in the case of secreted proteins. The specific productivity is calculated from the quotient of the concentration of the product in the medium (=titre, determined by ELISA, for example) and the number of producing cells present over the time span under consideration, also known as the "IVC" (integral of the number of living cells over time). The specific productivity is usually given in 'pcd' (=pg/cell*day=picograms of secreted protein per cell and per day)).

The term "serum-free" means culture media and also cultivation conditions which are characterised in that cells are grown in the absence of animal and/or human serum, preferably in the absence of any proteins isolated from serum, preferably in the absence of non-recombinantly produced proteins. Consequently, the term "cells adapted to serum-free conditions" means those cells which can be multiplied in the absence of animal or human serum or serum proteins.

The term "protein-free" means that the culture medium does not contain any animal proteins; proteins isolated from bacteria, yeasts or fungi are not regarded as animal proteins.

The term "chemically defined" describes a cell culture medium which is serum-free, preferably also protein-free, and which consists of chemically defined substances. Chemically defined media thus consist of a mixture of predominantly pure individual substances. One example of a chemically defined medium is the CD-CHO medium produced by Messrs Invitrogen (Carlsbad, Calif., US).

The expression "a cell which may be cultivated in suspension" refers to cells which are adapted to growth in liquid cultures ("suspension cultures") and whose ability to adhere to the surfaces of vessels, for example cell culture dishes or flasks, has been restricted or lost. Cells which are adapted both to serum-free growth and to growth in suspension are referred to as "non-adherent cells adapted to serum-free medium".

The term "gene of interest" or "recombinant gene of interest" encompasses a nucleotide sequence of any desired length that codes for a product of interest. The gene product or "product of interest" is generally a protein, polypeptide, peptide or fragment or derivative thereof. However, it may also be RNA or antisense RNA. The gene of interest may be full length, shortened, a fusion gene or labelled gene. It may be genomic DNA or preferably cDNA or corresponding fragments or fusions. The gene of interest may be the native gene sequence or may be mutated or otherwise modified. Such modifications include codon optimisations for adapting to a particular host cell and humanisation. The gene of interest may for example code for a secreted, cytoplasmic, nucleus-located, membrane-bound or cell surface-bound polypeptide.

The term "product of interest" refers to biopharmaceutically significant substances such as proteins/polypeptides, but also to DNA and RNA molecules (such as for example siRNA, antisense RNA) and other products such as e.g. viruses, viral particles, etc.

The term "protein of interest" relates to biopharmaceutically significant proteins/polypeptides comprising e.g. antibodies, enzymes, cytokines, lymphokines, adhesion molecules, receptors and the derivatives or fragments thereof. However, a protein/product of interest is not restricted to these examples. Generally, all polypeptides that act as agonists or antagonists and/or have a therapeutic or diagnostic use are significant or of interest. Other proteins of interest are for example proteins/polypeptides that are used to alter the properties of host cells within the scope of so-called "cell engineering", such as e.g. anti-apoptotic proteins, chaperones, metabolic enzymes, glycosylation enzymes, and the derivatives or fragments thereof, but are not restricted thereto.

The term "polypeptides" is used for amino acid sequences or proteins and refers to polymers of amino acids of any length. This term also includes proteins which have been modified post-translationally by reactions such as glycosylation, phosphorylation, acetylation or protein processing. The structure of the polypeptide may be modified, for example, by substitutions, deletions or insertions of amino acids and fusion with other proteins while retaining its biological activity. In addition, the polypeptides may multimerise and form homo- and heteromers.

By recombinant proteins are meant proteins that are produced by recombinant expression in host cells. Such recombinant proteins are produced under the strictest conditions of purity in order to minimise the risk of contamination. Recombinant proteins are usually produced in suitable host cells such as e.g. yeast cells, animal cells or prokaryotic cells (*E. coli* or other bacterial strains) using an expression vector such as for example a plasmid, bacteriophage, naked DNA or a virus, to introduce the recombinant protein into the host cell.

A recombinant protein is coded by a recombinant gene and expressed by a recombinant cell. Recombinant proteins are usually commercially available in purified form as concentrated protein solutions or in powder form. Recombinant HSA is obtainable for example from various commercial suppliers such as Sigma Aldrich. Examples of therapeutic proteins are insulin, insulin-like growth factor, human growth hormone (hGH) and other growth factors, receptors, tissue plasminogen activator (tPA), erythropoietin (EPO), cytokines, e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN)-alpha, -beta, -gamma, -omega or -tau, tumour necrosis factor (TNF) such as TNF-alpha, -beta or -gamma, TRAIL, G-CSF, GM-CSF, M-CSF, MCP-1 and VEGF. Other examples are monoclonal, polyclonal, multispecific and single chain antibodies and fragments thereof such as for example Fab, Fab', F(ab')2, Fc and Fc' fragments, light (L) and heavy (H) immunoglobulin chains and the constant, variable or hypervariable regions thereof as well as Fv and Fd fragments. The antibodies may be of human or non-human origin. Humanised and chimeric antibodies are also possible.

Fab fragments (fragment antigen binding=Fab) consist of the variable regions of both chains which are held together by the adjacent constant regions. They may be produced for example from conventional antibodies by treating with a protease such as papain or by DNA cloning. Other antibody fragments are F(ab')2 fragments which can be produced by proteolytic digestion with pepsin.

By gene cloning it is also possible to prepare shortened antibody fragments which consist only of the variable regions of the heavy (VH) and light chain (VL). These are known as Fv fragments (fragment variable=fragment of the variable part). As covalent binding via the cysteine groups of the constant chains is not possible in these Fv fragments, they are often stabilised by some other method. For this purpose the variable region of the heavy and light chains are often joined together by means of a short peptide fragment of about 10 to 30 amino acids, preferably 15 amino acids. This produces a single polypeptide chain in which VH and VL are joined together by a peptide linker. Such antibody fragments are also referred to as single chain Fv fragments (scFv). Examples of scFv antibodies are known and described.

In past years various strategies have been developed for producing multimeric scFv derivatives. The intention is to produce recombinant antibodies with improved pharmacokinetic properties and increased binding avidity. In order to achieve the multimerisation of the scFv fragments they are produced as fusion proteins with multimerisation domains. The multimerisation domains may be, for example, the CH3 region of an IgG or helix structures ("coiled coil structures") such as the Leucine Zipper domains. In other strategies the interactions between the VH and VL regions of the scFv fragment are used for multimerisation (e.g. dia-, tri- and pentabodies).

The term diabody is used in the art to denote a bivalent homodimeric scFv derivative. Shortening the peptide linker in the scFv molecule to 5 to 10 amino acids results in the formation of homodimers by superimposing VH/VL chains. The diabodies may additionally be stabilised by inserted disulphide bridges. Examples of diabodies can be found in the literature.

The term minibody is used in the art to denote a bivalent homodimeric scFv derivative. It consists of a fusion protein which contains the CH3 region of an immunoglobulin, preferably IgG, most preferably IgG1, as dimerisation region. This connects the scFv fragments by means of a hinge region, also of IgG, and a linker region.

The term triabody is used in the art to denote a trivalent homotrimeric scFv derivative. The direct fusion of VH-VL without the use of a linker sequence leads to the formation of trimers.

The fragments known in the art as mini antibodies which have a bi-, tri- or tetravalent structure are also derivatives of scFv fragments. The multimerisation is achieved by means of di-, tri- or tetrameric "coiled coil" structures.

The term "antibody fusion" or "antibody fusion protein" denotes the fusion/coupling of a protein to an antibody or part of an antibody. In particular these include fusion proteins produced by genetic engineering, in which a therapeutic protein is coupled to the Fc part of an antibody, in order thereby to increase the half-life/stability of the protein in the serum. The term also encompasses antibody fusions consisting of a peptide and an antibody or part of an antibody.

Preferred host cells for the purposes of the invention are hamster cells such as BHK21, BHK TK-, CHO, CHO-K1, CHO-DUKX, CHO-DUKX B1 and CHO-DG44 cells or derivatives/descendants of these cell lines. Particularly preferred are CHO-DG44, CHO-DUKX, CHO-K1 and BHK21 cells, particularly CHO-DG44 and CHO-DUKX cells. Also suitable are mouse myeloma cells, preferably NS0 and Sp2/0 cells and derivatives/descendants of these cell lines.

Examples of hamster and mouse cells which can be used according to the invention are given in Table 1 that follows. However, derivatives and descendants of these cells, other mammalian cells including but not restricted to cell lines of humans, mice, rats, monkeys, rodents, or eukaryotic cells, including but not restricted to yeast, insect, bird and plant cells, may also be used as host cells for the production of biopharmaceutical proteins.

TABLE 1

Known production cell lines

| Cell line | Accession number |
|---|---|
| NS0 | ECACC No. 85110503 |
| Sp2/0-Ag14 | ATCC CRL-1581 |
| BHK21 | ATCC CCL-10 |
| BHK TK⁻ | ECACC No. 85011423 |
| HaK | ATCC CCL-15 |
| 2254-62.2 (BHK-21 derivative) | ATCC CRL-8544 |
| CHO | ECACC No. 8505302 |
| CHO-K1 | ATCC CCL-61 |
| CHO-DUKX (= CHO duk⁻, CHO/dhfr⁻) | ATCC CRL-9096 |
| CHO-DUKX B1 | ATCC CRL-9010 |
| CHO-DG44 | Urlaub et al., Cell 33[2], 405-412, 1983 |
| CHO Pro-5 | ATCC CRL-1781 |
| Lec13 | (Stanley P. et al, 1984). |
| V79 | ATCC CCC-93 |
| B14AF28-G3 | ATCC CCL-14 |
| HEK 293 | ATCC CRL-1573 |
| COS-7 | ATCC CRL-1651 |
| U266 | ATCC TIB-196 |
| HuNS1 | ATCC CRL-8644 |
| Per.C6 | (Fallaux, F.J. et al, 1998) |
| CHL | ECACC No. 87111906 |

According to the invention, recombinant mammalian cells, preferably rodent cells, most preferably murine cells such as NS0 and hamster cells such as CHO or BHK cells are particularly preferred.

It is preferable if the host cells are established, adapted and cultivated totally under serum-free conditions. Particularly preferably the host cells are additionally established, adapted and cultivated totally in a medium that is not only serum-free but also free from any animal proteins/peptides.

Examples of suitable nutrient solutions include commercially obtainable media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif., USA), CHO-S Invitrogen), serum-free CHO-Medium (Sigma) and protein-free CHO-Medium (Sigma).

The term "production cell" or "producer cell" or "production clone" denotes a cell that is used in a process for preparing a protein. In particular this includes genetically modified cells that are used for the industrial production of recombinant proteins. Within the scope of this invention, the term includes in particular genetically modified eukaryotic host cells which express a recombinant protein and are used to prepare this protein. This includes in particular monoclonal cell lines for the production of therapeutic proteins.

EMBODIMENTS ACCORDING TO THE INVENTION

The invention describes a method of optimising a biopharmaceutical production process comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, the said cell culture medium containing the following buffer component:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P \times 5H_2O$, Sod-β)
c) regulating the pH by means of a non-CO2-forming acid and/or alkali,
while during the bioprocess the $pCO_2$ is regulated with CO2, O2, N2 and/or a supply of air or using the speed of the stirrer.

The invention describes a method of regulating the $pCO_2$ comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, the said cell culture medium containing the following buffer component:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P \times 5H_2O$, Sod-β)
c) regulating the pH by means of a non-CO2-forming acid and/or alkali,
while during the bioprocess the $pCO_2$ is regulated with CO2, O2, N2 and/or a supply of air or using the speed of the stirrer.

The invention further describes a method of improving the reproducibility of bioprocesses with eukaryotic cells, characterised in that at least the following parameters are monitored: pCO2 profile, O2 profile, pH profile, temperature profile, speed and
a) wherein the cultivation of the cell takes place in a cell culture medium that contains 12 mmol/L or less of $HCO_3^-$ or $CO_3^{2-}$ ions, and
b) wherein said cell culture medium contains the following buffer components:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P \times 5H_2O$, Sod-β) and c) wherein the regulation of the pH is carried out using a non-CO2-forming acid and/or alkaline solution and
d) wherein during the bioprocess the $pCO_2$ is regulated with $CO_2$, $O_2$, $N_2$ and/or a supply of air or by the speed of the stirrer.

The invention further describes a method of regulating the pH, comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, the said cell culture medium containing the following buffer component:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P\times5H_2O$, Sod-β)
c) regulating the pH by means of a non-$CO_2$-forming acid and/or alkaline solution, while during the bioprocess the $pCO_2$ is regulated with CO2, O2, N2 and/or a supply of air or by the speed of the stirrer.

The invention further describes a method of increasing the titre/the specific productivity, comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, said cell culture medium containing the following buffer component:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P\times5H_2O$, Sod-β)
c) regulating the pH by means of a non-$CO_2$-forming acid and/or alkaline solution,
while during the bioprocess the $pCO_2$ is regulated with CO2, O2, N2 and/or a supply of air or by the speed of the stirrer.

The invention further relates to a method of improving the product quality, comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, said cell culture medium containing the following buffer component:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P\times5H_2O$, Sod-β)
c) regulating the pH by means of a non-$CO_2$-forming acid and/or alkaline solution, while during the bioprocess the $pCO_2$ is regulated with $CO_2$, $O_2$, $N_2$ and/or a supply of air or by the speed of the stirrer.

The invention further relates to a method of improving the robustness of the process, comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, said cell culture medium containing the following buffer component:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P\times5H_2O$, Sod-β)
c) regulating the pH by means of a non-$CO_2$-forming acid and/or alkaline solution,
while during the bioprocess the $pCO_2$ is regulated with $CO_2$, $O_2$, $N_2$ and/or a supply of air or by the speed of the stirrer.

The invention further describes a method of preparing a recombinant product of interest comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, said cell culture medium containing the following buffer components:
  (i) N-tris(hydroxymethyl)methyl-2-aminoethanesulphonic acid ($C_6H_{15}NO_6S$, TES) and/or
  (ii) sodium-β-glycerophosphate-pentahydrate ($C_3H_7Na_2O_6P\times5H_2O$, Sod-β)
c) regulating the pH by means of a non-CO2-forming acid and/or alkaline solution,
while during the bioprocess the $pCO_2$ is regulated with CO2, O2, N2 and/or a supply of air or by the speed of the stirrer.

In a preferred embodiment of the production process according to the invention the product of interest is a protein, preferably an antibody or antibody fragment or Fc fusion protein.

In a preferred embodiment of one of the methods according to the invention as described above, the $pCO_2$ is regulated by the introduction of $CO_2$ and/or $N_2$ gas. Preferably, the $pCO_2$ is regulated exclusively by the introduction of $CO_2$ and/or $N_2$ gas.

In a preferred embodiment of one of the methods according to the invention as described above, the cell culture medium contains 8 mmol/L $HCO_3^-$ or $CO_3^{2-}$ ions.

In a particularly preferred embodiment of one of the methods according to the invention as described above the cell culture medium is completely free from $HCO_3^-$ or $CO_3^{2-}$ ions.

In a preferred embodiment of one of the methods according to the invention as described above the cultivation of the cell is carried out by the fed-batch fermentation method (and not e.g. by the perfusion method). Preferably, the cultivation of the cell is carried out by the fed-batch method. Preferably, from day 0 to the end of the fed-batch fermentation/fed-batch method no $HCO_3^-$ or $CO_3^{2-}$ ions whatsoever are added to and/or used in the medium.

In a specific embodiment of one of the methods according to the invention as described above the TES concentration is between 1 mmol/L and 100 mmol/L, 10-90, 20-80, 30-50 or less than or equal to 100 mmol/L or 40 mmol/L. A higher TES concentration than 100 mmol/L is not in accordance with the invention on account of the increasing osmolality.

In a specific embodiment of one of the methods according to the invention as described above the Sod-β concentration is between 1 mmol/L and 100 mmol/L, 5-50, 15-30 or less than or equal to 100 mmol/L or 25 mmol/L. A higher Sod-β concentration than 100 mmol/L is not in accordance with the invention on account of the increasing osmolality.

In a specific embodiment of one of the methods according to the invention as described above the acid and/or alkaline solution according to step c) is NaOH, HCl, $H_3PO_4$, $CH_3COOH$ or $H_2SO_4$, preferably NaOH or HCl.

In a specific embodiment of one of the methods according to the invention as described above the eukaryotic cell is a mammalian cell, preferably a rodent cell, preferably a CHO, PER.C6 or NS0 cell. In a specific embodiment of one of the methods according to the invention as described above the eukaryotic cell is a CHO, PER.C6 or NS0. In a preferred embodiment of one of the methods according to the invention as described above the $pCO_2$ is regulated in the initial growth phase (day 0 to day 3 or day 1 to 3, particularly on day 1 of the fermentation) to a value of less than or equal to 10% or less than or equal to 8%, preferably the $pCO_2$ is adjusted to a value of between 2% and 8% or between 3% and 8% or between 5% and 8% or between 3% and 5%, while a $pCO_2$ value of 5% or 3% is particularly preferred.

In another preferred embodiment the $pCO_2$ profile from day 0 to day 11 (or to the end of the fermentation) is set to 3% $pCO_2$. Preferably the $pCO_2$ is regulated to 3% from day 0 to day 11 (or to the end of the fermentation).

In another preferred embodiment the method further comprises that the $pCO_2$ value is additionally regulated as follows:
i) an average $pCO_2$ (less than or equal to 12%) in the growth phase (for example day 3-7 or day 4-8), of preferably 5-12% or 8-12%, particularly preferably 8-10% or 5-11% or 3-11%,
ii) a slightly elevated or high $pCO_2$ (greater than or equal to 5%, 8% or 15%) in the dying-off phase (day 7 to 11 or day 9-11 or up to the end of the (fed-batch) fermentation/up to the end of the cultivation of the cell/), of preferably 15-18% or 5-10% or 15%.

The invention further relates to a cell culture medium which contains 12 mmol/L or less of $HCO_3^-$ or $CO3^{2-}$ ions, said cell culture medium containing the following buffer components:
(i) N-tris(hydroxymethyl)methyl-2-aminoethanesulphonic acid ($C_6H_{15}NO_6S$, TES) and/or
(ii) sodium-β-glycerophosphate-pentahydrate ($C_3H_7Na_2O_6P\times 5H_2O$, Sod-β).

The invention describes in particular a fed-batch cell culture medium which contains 12 mmol/L or less of $HCO_3^-$ or $CO3^{2-}$ ions, said cell culture medium containing the following buffer components:
(i) N-tris(hydroxymethyl)methyl-2-aminoethanesulphonic acid ($C_6H_{15}NO_6S$, TES) and/or
(ii) sodium-β-glycerophosphate-pentahydrate ($C_3H_7Na_2O_6P\times 5H_2O$, Sod-β).

In a specific embodiment of the cell culture medium according to the invention the cell culture medium contains 8 mmol/L $HCO_3^-$ or $CO_3^{2-}$ ions.

In a specific embodiment of the cell culture medium according to the invention the cell culture medium is completely free of $HCO_3^-$ or $CO_3^{2-}$ ions.

In a specific embodiment the cell culture medium according to the invention is for the fed batch cultivation of cells. Preferably In a specific embodiment of the cell culture medium according to the invention the cultivated cells are eukaryotic cells, particularly mammalian cells, particularly rodent cells, particularly hamster cells, particularly CHO cells.

In a specific embodiment of the cell culture medium according to the invention the TES concentration is between 1 mmol/L and 100 mmol/L, 10-90, 20-80, 30-50 or less than or equal to 100 mmol/L or 40 mmol/L. A higher TES concentration than 100 mmol/L is not in accordance with the invention on account of the increasing osmolality.

In a specific embodiment of the cell culture medium according to the invention the Sod-βconcentration is between 1 mmol/L and 100 mmol/L, 5-50, 15-30 or less than or equal to 100 mmol/L or 25 mmol/L. A higher Sod-β concentration than 100 mmol/L is not in accordance with the invention on account of the increasing osmolality.

The invention further describes a fed-batch fermentation set-up or a set of fed-batch fermentation equipment, or kit, comprising the following components:
(a) cell culture medium which contains 12 mmol/L or less of $HCO_3^-$ or $CO3^{2-}$ ions, or which is preferably completely free from $HCO_3^-$ or $CO_3^{2-}$ ions, the said cell culture medium containing the following buffer components:
(i) N-tris(hydroxymethyl)methyl-2-aminoethanesulphonic acid ($C_6H_{15}NO_6S$, TES) and/or
(ii) sodium-β-glycerophosphate-pentahydrate ($C_3H_7Na_2O_6P\times 5H_2O$, Sod-β),
(b) fed-batch fermenter,
(c) eukaryotic cell, preferably a mammalian cell, rodent cell, hamster cell, most preferably a CHO cell.

Preferably, the cell in (c) is a recombinant cell. A recombinant cell contains a recombinant (e.g. an exogenous) DNA or RNA sequence which is preferably expressed and particularly preferably purified and isolated. Preferably, this recombinant cell expresses a gene of interest, particularly a therapeutic protein, preferably an antibody, an antibody fragment or an Fc fusion protein.

All the methods according to the invention are synonymously referred to as processes. Thus, the invention also relates for example to a process for regulating the $pCO_2$ comprising the following steps:
a) preparing a eukaryotic host cell which contains a recombinant gene of interest and produces a corresponding product of interest,
b) cultivating the cell from step a) in a cell culture medium which contains 12 mmol/L or less of $HCO_3^-$ or $CO_3^{2-}$ ions, said cell culture medium containing the following buffer component:
(i) N-tris(hydroxymethyl)methyl-2-aminoethanesulphonic acid ($C_6H_{15}NO_6S$, TES) and/or
(ii) sodium-β-glycerophosphate-pentahydrate ($C_3H_7Na_2O_6P\times 5H_2O$, Sod-β)
c) regulating the pH by means of a non-$CO_2$-forming acid and/or alkaline solution, while during the bioprocess the $pCO_2$ is regulated with $CO_2$, $O_2$, $N_2$ and/or a supply of air or using the speed of the stirrer.

In a preferred embodiment of one of the processes according to the invention as described above, the $pCO_2$ is regulated exclusively by the introduction of $CO_2$ and/or $N_2$ gas.

EXPERIMENTAL SECTION

Equipment and Methods

Fermentation

The experiments carried out were performed either in a bioreactor with a fermentation volume of 2 L (seed volume 1.8 L), in 250 ml shake flasks (seed volume 50 ml) or using a SensorDish Reader® made by the company Presents (seed volume 1.5 ml).

Experiments with the bioreactor have numerous advantages such as data capture in real time and archiving of the process parameters, an established and valid regulation of the process variables of temperature, pH, gas supply (different proportions of gases) and stirrer speed. The data obtained can be reproduced by means of the controlled conditions and can be transferred to larger bioreactors (scale-up/scaling). The yields in the bioreactor are generally higher, by comparison, than with alternative fermentation methods. This results inter alia from the integrated stirrer with its turbulent mixing action that provides a better supply of nutrients and an increased introduction of oxygen. However, operation is relatively complicated and time-consuming, as at the beginning the fermentation apparatus/equipment has to be put together and sterilised, during the fermentation daily supervision is required and after the fermentation the equipment has to be taken apart and carefully cleaned. Operation is thus very labour-intensive and costly.

Bioreactors are used for fermentation when good results have already been obtained in preliminary tests and the additional advantages of a bioreactor are required.

For bioreactors there are different operating modes. Whereas a batch process is primarily characterised by a constant volume, this is variable in a fed-batch process. Variable because during the fermentation process there are additions to the cell culture liquor. Additions may be a fed in continuously or in the form of an additional bolus to assist the fermentation process.

In the fermentations using the bioreactor described in the experimental section, fed-batch processes were used.

The cultivation of cells in shake flasks has the advantage that it can be carried out with relatively simple means. In addition to an incubator, an LAF box (laminar flow, sterile working area) and the disposable flask no other technical equipment is required. The flasks are filled under sterile conditions with cell culture medium and inoculum of a defined concentration and then transferred into the incubator. The cell culture can be influenced by adjusting the settings on the incubator (desired temperature, relative humidity, speed and —$CO_2$ content). As the shake flasks are delivered in sterile packaging, no other preparation of the equipment is required. However, the disadvantages are obvious: it is not possible to carry out online data capture, regulate the pH, introduce gas or carry out a feed. The sampling for analysis and the addition of feed and bolus has to be carried out under the LAF box. This is a source of contamination or errors and in addition to routine handling takes up a great deal of time. Moreover, from the point of view of analysis, the sample volume imposes restrictions: For example, at the start of fermentation, 50 ml are seeded, and for every sample an amount of two to three milliliters is taken (generally daily). Although this is partly compensated by the addition of feed and bolus, this is a major removal on each occasion, in relation to the total volume of the culture. Generally, tests in inexpensive shake flasks are highly suitable as a precursor for bioreactor tests, on account of their ease of handling and good evaluation possibilities.

Experiments using a Sensor Dish Reader (=SDR) partly combine the advantages of bioreactors and shake flasks. In this method, a 24-well dish is seeded with only 1.5 ml of cell suspension per well and the dish is covered and placed in the incubator. A sensor point is applied to the underside of each well. Under the well plate is the so-called reader which reads out this sensor. This allows non-invasive measurement of pH or $pO_2$ online and in real time. No prior calibration is required; the calibration data are automatically loaded into the control software at the start using the printed batch number.

However, the possibilities of SDR are limited to reading the pH in the well and drawing conclusions as to the cell growth by interpreting the drop in $pO_2$ over time. The process is recommended for testing toxicities, effects of individual substances or threshold concentrations. SDR is also useful in tests that require multiple measurements. As there is no sampling and the experiment has a running time of only three days and thus there is no need for any feeding either, this method saves a great deal of time and allows very comfortable handling.

pH Regulation

In the tests with the Sensor Dish Reader and during fermentation in shake flasks in the incubator no active pH regulation is carried out.

The pH regulation in the bioreactor is regularly carried out at BI by the addition of $Na_2CO_{3(aq)}$ and $CO_{2(gas)}$. The regulation is carried out automatically using SimaticIT® (see the section on software). Where $pH_{actual} > pH_{desired}$, $CO_{2(gas)}$ is introduced, where $pH_{actual} < pH_{desired}$, $Na_2CO_{3(aq)}$ is metered in through a regulated pump until the desired value, +/− defined deadband, is reached again.

In the present instance, in some fermentations, for the reasons stated, $Na_2CO_{3(aq)}$ is replaced by sodium hydroxide solution which has an equivalent effect.

Media

As the basic cell culture medium a BI proprietary medium is used as the standard medium in all the fermentations. Media A and B differ only in the preselected pH. Both media are serum-free production media which are produced in-house on a "just in time" basis.

The feed medium used is also a BI proprietary feed medium produced in-house. A feed medium generally contains highly purified water (WFI=water for injection), glucose, amino acids, growth factors and biological extracts from e.g. yeasts that are ideal for the particular cell line. In the multifermentations the feed medium is supplied continuously by means of a pump, while in the fermentations in the shake flasks it is pipetted in by hand under the LAF box.

For the experiments in the bioreactor a so-called multifermenter is used. It consists of six identical individual fermenters each with a fermentation volume of two liters, which are physically combined to form a portable unit. The equipment is actuated with PCs using SimaticIT® software. The basic structure of the fermenter is formed by the 2 L glass container with double jacket for temperature control and the cover plate into which the probes and other peripheral equipment such as riser tubes, for example, are screwed.

In the fermentation in the bioreactor, the following probes are used that are screwed into the cover plate of the bioreactor: temperature probe, $pO_2$ probes, pH probe, $CO_2$ probe.

For all the fermentations carried out a BI-HEX® cell is used. BI-HEX® stands for Boehringer Ingelheim High Expression System. The BI-HEX® cell is a CHO cell, the genetic construct of which is altered/optimised so that a product of interest is effectively produced. When cells are needed, an ampoule with the corresponding CHO cells from the inoculum sector is thawed out, expanded and a stock culture is applied in order to ensure expansion for seeding in the bioreactor or shake flask. The cell secretes a certain biomolecule, preferably a protein, preferably a specific antibody extracellularly into the cell culture medium. This is detected when the concentration of the titre is determined.

Example 1

SDR Experiment (Reduction in $NaHCO_3$ Concentration)

The elementary function of $NaHCO_3$ for the cell has already been described. This experiment is intended to show how, or whether, reduced $NaHCO_3$ concentrations have an effect on cell growth. The evaluation is made by drawing conclusions as to the oxygen consumption (by cell growth) in the cell culture medium. The experiment is carried out on a SensorDish Reader.

The test series was carried out with n=4 so as to be able to detect outliers and evaluate the general scatter. A 24-well OxiDish OD24 plate is used. In addition to the five different $NaHCO_3$ concentrations a test series with a specific concentration of $NaHCO_3$ and HEPES is run. This combination is described in the literature, although it is only run with 3% $pCO_2$ in that instance. The present experiment (6) is run with 5% $pCO_2$, so as to achieve comparability with other experiments. For more information see the experimental plan in Table 1.

In order to keep the variance as low as possible, the cell suspension for a test series of the same concentration is produced in the pool, pipetted into the wells and then provided with the calculated, identical volume of $NaHCO_3$ stock solution.

| | |
|---|---|
| Platform: | SensorDish Reader (SDR) |
| Cell: | CHO |
| Run time: | 90 h |
| Medium: | MEDIUM A w/o $NaHCO_3$ + weighed amount/ stock solution buffer substance |
| Feeding: | -not applicable- |
| T/L: | 36.8° C./70% |
| $CO_2$ profile: | constant 5% |
| Seeding density: | 0.6 |

TABLE 1

| Test series No. | buffer substance(s)/concentration | repeats (n) |
|---|---|---|
| 1 | $NaHCO_3$/A | 4 |
| 2 | $NaHCO_3$/B | 4 |
| 3 | $NaHCO_3$/C | 4 |
| 4 | $NaHCO_3$/D | 4 |
| 5 | $NaHCO_3$/D + HEPES/E | 4 |
| 6 | control MEDIUM A (containing $NaHCO_3$)/F | 4 |

| $NaHCO_3$ | | HEPES | |
|---|---|---|---|
| mmol/L | Standardised data | mmol/L | Standardised data |
| 0 | A | 0 | A |
| 1 | B | 20 | E |
| 4 | C | | |
| 8 | D | | |
| 36 mmol | (Ktr)/F | | |

In test series number five, in addition to $NaHCO_3$, HEPES is also added to the pool by means of stock solution.

For evaluation, the diagram in FIG. 1 is used, in which the $pO_2$ values of each well are recorded against the time. The diagram has already been purged of an outlier in test series four and is based on the arithmetical averages of the fourfold repetition (3-fold in test series four).

The reduced $NaHCO_3$ concentration of 8 mmol/L shows an advantageous $pO_2$ profile similar to the control (cell growth).

Example 2

Shake Flask Experiment

The selection of the buffer systems (cell-free) is now operated with cells. The criterion for the choice of the buffer systems used in this experiment is an acceptable osmolality and good buffer characteristics during the introduction of gas into the shake flask incubator. The test setup/experiment plan goes with the finding in Example 1 that even with an $NaHCO_3^-$ concentration reduced to concentration D (=8 mmol/L) good growth rates (deduced from the oxygen consumption) can be obtained.

The objective is to determine the best buffer medium, in relation to the growth performance of the cell, as a basis for a subsequent fermentation in the bioreactor.

The preparation is carried out analytically as precisely as possible. The pH values are adjusted by BGA comparison. Lower buffer concentrations are added by means of stock solutions. After manufacture, sterile filtration is carried out. As a safety measure the experiments are carried out with n=2. To achieve two different gas supply variants, the experiments are split between two different incubators. A summary can be found in the experiment plan.

| | |
|---|---|
| Platform: | Shake flasks in the incubator |
| Cell: | CHO |
| Run time: | 11 d |
| Medium: | MEDIUM A w/o $NaHCO_3$ w/o MOPS + weighed amount/stock solution buffer substance |
| Feeding: | 1.5 ml/day |
| T/L: | 37° C./70% |
| $CO_2$ profile: | see experiment plan |
| Seeding density: | 1.1 |

TABLE 2

Experiment plan, Incubator 1
Incubator 1
$CO_2$ profile d0-d3: 5%; d3-d11: 3%

| No. | Buffer subst./conc. |
|---|---|
| SF0 | HEPES/I |
| SF0 | HEPES/I |
| SF0 | HEPES/G |
| SF0 | HEPES/G |
| SF0 | MOPS/I |
| SF0 | MOPS/I |
| SF0 | MOPS/F |
| SF0 | MOPS/F |
| SF0 | Sod-β/F |
| SF1 | Sod-β/F |
| SF1 | Sod-β/H |
| SF1 | Sod-β/H |
| SF1 | TES/U |
| SF1 | TES/U |
| SF1 | TES/K |
| SF1 | TES/K |
| SF1 | Trizma base/F |
| SF1 | Trizma base/F |
| SF1 | Trizma base/I |
| SF2 | Trizma base/I |
| SF2 | MEDIUM A (Ktr) |
| SF2 | MEDIUM A (Ktr) |
| SF2 | Blank |
| SF2 | Blank |
| SF49 | HEPES/G +$NaHCO_3$/D |
| SF50 | MOPS/F + $NaHCO_3$/D |
| SF51 | Sod-β/H + $NaHCO_3$/D |
| SF52 | TES/K + $NaHCO_3$/D |
| SF53 | Trizma base/F+ |

Shown here: In each case the lower concentration of the buffer substance plus the optimum $NaHCO_3$ concentration deviating from the standard (D = 8 mmol/L); n = 1

TABLE 3

Experiment plan, Incubator 2
Incubator 2
$CO_2$ profile d0-d3: 3%; d3-d11: 0%

| No. | Buffer subst./conc. |
|---|---|
| SF2 | HEPES/I |
| SF2 | HEPES/I |
| SF2 | HEPES/G |
| SF2 | HEPES/G |
| SF2 | MOPS/I |
| SF3 | MOPS/I |
| SF3 | MOPS/F |
| SF3 | MOPS/F |
| SF3 | Sod-β/F |
| SF3 | Sod-β/F |
| SF3 | Sod-β/H |
| SF3 | Sod-β/H |
| SF3 | TES/U |
| SF3 | TES/U |
| SF3 | TES/K |
| SF4 | TES/K |
| SF4 | Trizma base/F |
| SF4 | Trizma base/F |
| SF4 | Trizma base/I |
| SF4 | Trizma base/I |
| SF4 | MEDIUM A (Ktr) |
| SF4 | MEDIUM A (Ktr) |
| SF4 | Blank |
| SF4 | Blank |
| SF54 | HEPES/G + $NaHCO_3$/D |
| SF55 | MOPS/F + $NaHCO_3$/D |
| SF56 | Sod-β/H + $NaHCO_3$/D |
| SF57 | TES/K + $NaHCO_3$/D |
| SF58 | Trizma base/F+ |

Shown here: In each case the lower concentration of the buffer substance plus the optimum $NaHCO_3$ concentration deviating from the standard (D = 8 mmol/L); n = 1

The analysis on d0 (day 0) was carried out immediately after the seeding under the LAF box, i.e. without any previous effect of the $CO_2$ atmosphere of the incubator.

FIG. 2A shows that all the buffer medium mixtures apart from Trizma base (SF19 and SF20) with concentration I show some cell growth. The best growth is seen in the two controls (SF21 and SF22), but the difference from the buffer medium mixtures, at least up to d8, is relatively small. The three best buffers, with a cell density in the range of 45, are Sod-β/H; TES/K+$NaHCO_3$/D and MOPS/F+$NaHCO_3$/D. Trizma base runs poorly in any concentration, the pH is certainly stable but there may be some toxicity.

In FIG. 2B the same scale has been used as in FIG. 2A. It is clear that the cell densities achieved are considerably lower with this $CO_2$ profile. Admittedly, the controls perform best here too, but a maximum cell density of 20 is unacceptable. The best two buffer mixtures with a cell density in the region of 18 are in this case Sod-β/H+$NaHCO_3$/D and MOPS/F. For this reason the further evaluation is restricted primarily to the shake flasks from incubator 1 with the associated $CO_2$ profile.

Generally, the combination with $NaHCO_3$/D at the low buffer concentrations is advantageous.

When the $pCO_2$ measurement is carried out it is found that the prescribed $pCO_2$ profile is maintained. It is apparent that the later the timing of the sampling, the lower is the $pCO_2$ measured. This is a result of opening the incubator repeatedly.

The controls show, in incubator 1 towards the end, another rise in the $pCO_2$, which presumably results from the production within the cells.

The progression of the pH over the fermentation period is also measured. The pH values are at an acceptable level. The controls (SF21 and SF22) are still above the actual starting value of 7.00+/−0.05 on day 2 (d2). This could be due to the deviation from the pH meter compared with the BGA; the control was obtained directly, without any interference, from the manufacture of the media, where the pH is selected without BGA. In the controls the pH value falls most sharply at the end, based on the acidification of the cell culture.

FIG. 2C shows the titre concentrations achieved (standardised). With a few exceptions an increasing titre can be detected between d8 and d11. The gain in the shake flasks SF49 to SF52, the media with the reduced $NaHCO_3$ concentration, may even be more than tenfold!

Another remarkable fact is that for the first time with a new buffer substance in the medium, the conventional control (SF21 and SF22) has been outperformed: SF52 with TES/K+$NaHCO_3$/D yield a very good result on d11 with a standardised product concentration of 83.6.

Result:
Identification of the best buffer substances in $NaHCO_3$-free cell culture medium (left-hand half of the Table) or in reduced-$NaHCO_3$ (=8 mmol/L) cell culture medium (right-hand half of the Table).
The best buffer substances were: TES and Sod-β

Example 3

Bioreactor Fermentation

Test Set-Up $pCO_2$ Regulation:

There are different types of regulators available in different combinations for regulating a process. They may comprise the following regulators:

1. P-regulators: Proportional regulators. These are used in applications that have low demand for accuracy of regulation. P-regulators have a constant regulating deviation.
2. I-regulators: Integral regulators. These are used in applications that have low demand for speed of regulation but are very accurate.

In practice PI regulators are used most frequently and also in the present fermentation control. PI regulators combine the advantages of P and I regulators: they regulate speedily by means of the P content, and accurately and without any permanent regulating deviation by means of the I content; the effects of the individual regulators are added together.

The regulating characteristics are intended to be optimised in the subsequent course of the fermentation by modification of the regulating settings (P-I components).

The bioreactor contains the following components:

TABLE 4

| No. | name | function |
|---|---|---|
| 1 | temperature probe | measuring temperature in the bioreactor. |
| 2 | gassing filter | sterile barrier between incoming gas mixture and bioreactor. |
| 3 | gassing tube | nozzle at lower end releases gas bubbles. |
| 4 | exhaust connector | evacuation of air from bioreactor. |
| 5 | surface addition port 1 | organic solutions such as glucose, glutamine and feed are added through the triple distributor. |
| 6 | cell & PBS addition port | filling the bioreactor with inoculum and buffer. |
| 7 | surface addition port 2 | chemical solutions such as antifoam and pH adjuster are added through triple distributor |
| 8 | sample port | samples taken using sterile disposable syringe. |
| 9 | $CO_2$ probe | measuring the $PCO_2$ in the bioreactor. |
| 10 | $O_2$ probe | measuring the $pO_2$ in the bioreactor. |
| 11 | pH probe | measuring the pH in the bioreactor. |

The modified bioreactor contains, in particular, an integrated $CO_2$ probe. The hardware set-up of the experiments can, however, be varied, in principle, to meet different requirements. For example, a riser tube may be omitted and instead another probe may be installed or further/other solutions may be added automatically through hose pumps.

The $pCO_2$ measurements show first of all that the regulator oscillates for a long time after changes to the desired value. From the moment of seeding until the desired value of 8% has been achieved the regulator oscillates for about two days. When the desired value is lowered from 8% to 6% the regulator oscillates for another 14 hours; after in-process calibration, for about 12 hours.

The gas volume flows that apply at the maximum negative control variable (−45%) of the $pCO_2$ regulator are also measured. In spite of this control variable the desired value of 2% $pCO_2$+0.3% is not achieved. From this it can be concluded that with a $pCO_2$ desired value of 2% a critical lower limit is reached which does not appear to be useful in the process. As the nitrogen introduced expels the oxygen, this has to be compensated by an increased volume flow of oxygen. The accumulated total gas volume flow may reach a critical magnitude with regard to foaming. It is also clear that after the regulation has settled at a higher level a uniform supply of $CO_2$ gas is obtained.

In FIG. 3 the $pCO_2$ online data (corresponding to the $pCO_2$ probe measurement archived minute by minute) are compared with the values measured externally after sampling on the BGA. The first calibration is not very successful, as it shows a constant difference. However, after the second calibration, the measurements that follow agree. From this it can be concluded that in-process calibration only makes sense when the oscillating regulating characteristics have abated. In the second quarter of the fermentation the external measured values are higher. The hypothesis for this is that at this time the cell metabolism is highly active and a great deal of $CO_2$ is formed. In the sample in the syringe that is no longer being supplied with gas, $CO_2$ can then accumulate until it is measured.

FIG. 3 thus graphically shows the course of the internal measurement of $pCO_2$ (probe with automatic data archiving) and of the external measurement on the blood gas analyser. The first calibration marked with an arrow (comparison between $CO_2$ probe and BGA) on day 0 (d0) shows little effect, as the regulating characteristics are still too unsettled. From the 2nd calibration onwards (2nd arrow) on day 4 (d4) good agreement can be found between the internal and external measurements.

A function test carried out beforehand shows that the oscillation of the $pCO_2$ regulation is dependent on the buffer system. In the $pCO_2$ regulation in PBS buffer, carried out as a test, the regulating system is stable after only three hours.

The fermentation using the multifermenter is again preceded by an optimising test using SDR. In this preliminary test, in accordance with Example 1, different $NaHCO_3$ concentrations are tested in conjunction with the media Sod-β/H and TES/K. In the experiment, in addition to the evaluation by the drop in $pO_2$, an identically covered well plate is used having pH sensors. The results serve to make the decision for the current Example, the most promising combinations (TES/K+$NaHCO_3$/D and Sod-β/H+$NaHCO_3$/E) are included in the experiment plan. (The data from the preliminary test are not shown here.)

Fermentation takes place in two multifermenters (corresponding to twelve individual fermenters) with different media combinations.

The procedure and handling are based on the sections described under the headings Equipment, Methods and Operating steps. The test set-up and the experiment plan are summarised in Table 5.

| | |
|---|---|
| Platform: | Bioreactor/Multifermenter |
| Cell: | CHO |
| Run time: | 11 d (11 days) |
| Medium: | MEDIUM B w/o $NaHCO_3$ + weighed amount/stock solution buffer substance(s) |
| Feeding: | From dx continuous feed |
| T: | 37.0° C. |
| Seeding density: | 1.7 |
| $CO_2$-profile: | d0 to d3: 8%-d3 to d6: 6%-d6 to d8: 2%-d8 to d11: 4% |

The $CO_2$ profile shown above applies to the regulated bioreactor FS 33.1. in the remaining fermenters, after the seeding (d0), for a specific length of time at a specific control magnitude, $CO_{2(gas)}$ is added in order to provide the cells with a minimum of dissolved $CO_2$. Further $pCO_2$ measurements were carried out on d1, in the course of which it was found that on average the cultures contained about 2 to 3% $CO_2$. In the context of determining cell density it was jointly decided that no further manual interventions are required for supplying $CO_2$ gas.

The regulating characteristics were observed once again. In order to allow an objective assessment to be made at a later stage, no settings were altered or manual interventions made. The analysis of the regulating characteristics is intended to serve as the basis for the separate regulator adjustment (in future, separate positive and negative adjustment ranges).

TABLE 5

Experiment plan

| FS | buffer substance(s)/concentration | pH agents | $pCO_2$-Management |
|---|---|---|---|
| 32.1 | TES/K | $CO_2$/NaOH | defined initial gassing(d0) |
| 32.2 | TES/K + $NaHCO_3$/D | $CO_2$/NaOH | defined initial gassing(d0) |
| 32.3 | TES/K + $NaHCO_3$/D | $CO_2$/$Na_2CO_3$ | defined initial gassing(d0) |
| 32.4 | Sod-β/H | $CO_2$/NaOH | defined initial gassing(d0) |
| 32.5 | Sod-β/H + $NaHCO_3$/E | $CO_2$/NaOH | defined initial gassing(d0) |
| 32.6 | TES/K | $CO_2$/NaOH | no addition of $CO_2$ |
| 33.1 | TES/K | $CO_2$/NaOH | automatic regulation |
| 33.2 | Sod-β/H + $NaHCO_3$/E | $CO_2$/$Na_2CO_3$ | defined initial gassing(d0) |
| 33.3 | MEDIUM B ($NaHCO_3$/F) (comp. control) | $CO_2$/NaOH | defined initial gassing(d0) |
| 33.4 | MEDIUM B ($NaHCO_3$/F) (control) | $CO_2$/$Na_2CO_3$ | defined initial gassing(d0) |
| 33.5 | MEDIUM B ($NaHCO_3$/D) | $CO_2$/NaOH | defined initial gassing(d0) |
| 33.6 | MEDIUM B ($NaHCO_3$/D) | $CO_2$/$Na_2CO_3$ | defined initial gassing(d0) |

The fermentation systems (FS) 32.1, 32.6 and 33.6 unfortunately failed over the fermentation period because of contamination. The data obtained were not included, or were only included to a limited extent, in the consideration of the results.

Comparison of $pCO_2$ Regulated with $pCO_2$ Unregulated

As both FS 32.1 and FS 32.6, which like the regulated bioreactor FS 33.1 are operated with the cell culture medium TES/K, were ruled out on the grounds of contamination, the different can only be estimated by comparison with FS 32.2 and FS 32.3 (both TES/K+$NaHCO_3$/D). FIGS. 4 A and B on the normal viable cell count concentration (A) or titre concentration (B) show that the cell specific product formation rate of the regulated fermentation run (curve with triangular symbol) is higher than that of the comparable unregulated fermentation run (curve with diamond).

Moreover, the experiments from FIG. 4 show that the pH regulation with NaOH tends to have a better product formation rate than that using $Na_2CO_3$.

During further optimisation of the $pCO_2$ profile the specific product formation rate is increased further.

The viable cell count density of the $pCO_2$-regulated run (FS 33.1) deviates from one another by a maximum of 20 units, as shown in FIG. 4B. From d10 the two comparison runs also show only a slight divergence, otherwise good conformity is achieved. The lower level of FS 33.1 may result from the higher $pCO_2$ profile and should not be interpreted negatively. The vitality (not shown) is at the same level in all the runs.

The consumption of alkaline solution (not shown) is low in all the runs. In FS 32.2 (highest live cell count concentration) more alkaline solution has to be added towards the end of the fermentation (d9-d11) as expected. In spite of this, at the end of the fermentation this run has the lowest osmolality (not shown) at 393 mosmol/kg.

FIG. 4A shows that in spite of having a lower cell count than FS 32.3, FS 33.1 has a higher titre concentration. The concentration is in the upper third of the scatter between the two identical fermentation runs FS 32.2 and FS 32.3. This means that the fermentation run with the $pCO_2$ regulation has a higher specific product formation rate.

Comparison of Buffer Systems

The different buffer systems are then compared with one another.

FIG. 5A shows that the $pCO_2$ profile of the regulated fermentation run (FS33.1) differs significantly from the comparison fermentations (FS32.2 and FS32.3). FS32.2 and FS32.3 are used for the comparison even though they contain a small amount of $NaHCO_3$, as there is no identical comparison partner owing to contamination. The $pCO_2$ profile obtained by the regulation is clearly distinguished from the comparison runs in the first third of the fermentation and largely follows the prescribed values (cf. FIG. 5B, d1-d3 $pCO_2$=8%, d3-d6 $pCO_2$=6%, d6-d8 $pCO_2$=2% and from d8-d11 $pCO_2$=4%). When a lower than normal $pCO_2$ value is imposed (day 6-8, d6-d8) nitrogen gas is fed in so as to expel $CO_2$. It is found that the low desired value is never reached and a $pCO_2$ value of 3.2% represents a critical lower limit for the regulation. With the increased demand for nitrogen, oxygen is also expelled as a result, and this is compensated by a higher volume flow of oxygen. A critical total amount of gas can be achieved, in which an unreasonably large amount of foaming can be observed.

FIG. 5B shows that the regulated fermentation run is also surprisingly clearly distinguished from all the other comparison runs. This means that the $pCO_2$ profile achieved by regulation is actually based on the prescribed value (d1-d3 $pCO_2$=8%, d3-d6 $pCO_2$=6%, d6-d8 $pCO_2$=2% and from d8-d11 $pCO_2$=4%) and does not occur by accident.

FIG. 5C shows that the titre concentrations that are obtained with TES without $NaHCO_3$ or TES with 8 mmol/L $NaHCO_3$ are comparable with the control ($NaHCO_3$ based buffer with a concentration of 36 mmol/L). In spite of a randomly selected and non-optimised $pCO_2$ profile, the run with TES without $NaHCO_3$ (regulated) achieves a final concentration (titre) which differs from the control by only 6.10% (measured on the control). The run with TES plus 8 mmol/L $NaHCO_3$ (unregulated) achieves a final concentration (titre) which differs from the control by only 0.01% (measured on the control). This shows, totally surprisingly, that $NaHCO_3$ can be entirely replaced by TES. Moreover, it shows that the result of the run with TES plus 8 mmol/L $NaHCO_3$ (unregulated) achieves the same final titre concentration as the control.

Ideally a fermentation run takes place under the following conditions: TES buffer completely without $NaHCO_3$ and with $pCO_2$ regulation. The best end titres are achieved in this way.

Example 4

Fermentation Verification Buffer System

In six $CO_2$-regulated bioreactors the buffer systems TES and Sod-β are used with different concentrations of $NaHCO_3$, in order to determine the optimum concentration of $NaHCO_3$ in the medium. The test set-up is described below:

Platform: Bioreactor/Multifermenter
Method: Fed Batch
Cell: CHO
Seeding density: $3 \times 10^5$ vc/mL
Start volume: 1.8 L
Run time: 11 days
Medium: Medium B, $NaHCO_3$-free, MOPS-free+weighed amount/stock solution buffer substance(s)
Feeding: Feed I continuously from day 2
Temperature: 37° C.
$pO_2$: 60%
Speed: 160 rpm
pH: day 0-3 6.95±0.15, day 3-11 6.80±0.15
pH regulation: NaOH (1.2M) (no $CO_2$)
$pCO_2$: day 0-3 5%, day 3-11 3%

The buffer systems used with different concentrations of $NaHCO_3$ are shown in Table 6.

TABLE 6

Experiment plan showing buffer systems and $NaHCO_3$ concentrations used.

| Run | Buffer substance (concentration) | concentration of $NaHCO_3$ [M] |
|---|---|---|
| 1.1 | TES (40 mM) | — |
| 1.2 | TES (40 mM) | 8 |
| 1.3 | Sod-β (25 mM) | — |
| 1.4 | Sod-β (25 mM) | 8 |
| 1.5 | Sod-β (25 mM) | 12 |
| 1.6 | Sod-β (25 mM) | 16 |

The standardised product concentrations shown in FIG. 6 show no differences in the $NaHCO_3$ concentration used, when the same buffer substance is used. When TES is used (1.1, 1.2) identical product concentrations are produced by different $NaHCO_3$ concentrations. In the other fermentations using Sod-β (1.3, 1.4, 1.5, 1.6) and different concentrations of $NaHCO_3$ it is confirmed that the productivity of the cells is independent of the concentration of $NaHCO_3$ used in the medium. For this reason it is possible to cultivate cells without the use of $NaHCO_3$.

Example 5

Fermentation Comparison $CO_2$ Profiles

In five $CO_2$-regulated bioreactors different desired $CO_2$ values are prescribed over the cultivation period, in order to find the optimum $CO_2$ profile for a fermentation process.

The test set-up is described below:
Platform: Bioreactor/Multifermenter
Method: Fed Batch
Cell: CHO
Seeding density: $3 \times 10^5$ vc/mL Start volume: 1.8 L
Run time: 11 days
Medium: Medium B, NaHCO$_3$-free, MOPS-free+Sod-β (25 mM)
Feeding: Feed I continuously from day 2
Temperature: 37° C.
pO$_2$: 60%
Speed: 160 rpm
pH: day 0-3 6.95±0.15, day 3-11 6.80±0.15
pH regulation: NaOH (1.2M) (no CO$_2$)

The different CO$_2$ profiles of the six fermentation processes are shown in Table 7.

TABLE 7

Experiment plan with different CO$_2$ profiles.

| Run | CO$_2$ profile |
|---|---|
| 3.1 | day 0-3 5% CO$_2$, day 3-11 3% CO$_2$ |
| 3.2 | day 0-2 8% CO$_2$, day 2-11 6% CO$_2$ |
| 3.3 | day 0-4 8% CO$_2$, day 4-8 10% CO$_2$, day 8-11 8% CO$_2$ |
| 3.4 | day 0-1 8% CO$_2$, day 1-2 6% CO$_2$, day 2-7 8% CO$_2$, day 7-11 5% CO$_2$ |
| 3.5 | day 0-11 3% CO$_2$ |

As on day 0 it was omitted to take another sample for a CO$_2$ correction in the afternoon, the CO$_2$ values specified (cf. Table 6) from day 0 to 1 do not correspond to the measured values, as shown in FIG. 7C.

Both the standardised live cell concentrations and also the product concentrations of the individual processes with different pCO$_2$ profiles are largely similar apart from run 3.2. In process 3.2 the cells grow less well than in all the other processes (cf. FIG. 7A). Because of the poor cell growth and low cell density the product concentration in this run is lower than in the others (cf. Figure B). In relation to the CO$_2$ profile of run 3.2, FIG. 7C shows that this is the only run that has a high pCO$_2$ (>8%) on day 1.

Thus the cell growth is negatively affected by an initially high pCO$_2$.

Example 6

Shake Flasks Acid Tolerance Using the Na Salts

In 10 250 ml shake flasks, cells are tested for their acid tolerance with the addition of sodium salts. The salt solutions are selected such that the quantities of acids determined by titration beforehand are present in 1.5 ml of solution for a pH shift from 7.1 to 6.7. On day 3 these 1.5 ml of the different salt solutions are added to the shake flasks to simulate a pH shift.

The test set-up is described below:

| | |
|---|---|
| culture vessel/fill quantity: | 250 mL/50 mL |
| cell: | CHO |
| medium: | Medium B, NaHCO$_3$-free, MOPS-free + Sod-β (25 mM) |
| seeding density: | 2 × 10$^5$ vc/mL |
| cultivation period: | 11 days |
| cultivation conditions: | temperature: 37° C. |
| | relative humidity: 70% |
| | speed: day 0-3 120 rpm, day 3-7 140 rpm |
| | CO$_2$: day 0-3 5%, day 3-11 3% |
| Feeding: | Feed I daily 1.5 ml |

The different additions to the 10 shake flasks are shown in Table 8.

TABLE 8

| Shake flask | Addition |
|---|---|
| SF1 | water (for control) |
| SF2 | |
| SF3 | sodium chloride 23.4 g/L |
| SF4 | (for hydrochloric acid) |
| SF5 | sodium acetate 39.4 g/L |
| SF6 | (for acetic acid) |
| SF7 | sodium sulphate 34.1 g/L |
| SF8 | (for sulphuric acid) |
| SF9 | disodium hydrogen phosphate 61.7 g/L |
| SF10 | (for phosphoric acid) |

The standardised live cell concentrations shown in FIG. 8 show that the cells in all the shake flasks with the exception of SF 5 and 6 grow similarly, with the addition of sodium acetate. In these shake flasks, lower cell concentrations are achieved and the cells start to die off on day 7, so that the addition of sodium acetate results in significantly poorer growth. Thus, the use of acetic acid for pH adjustment in the bioreactor can be ruled out.

Example 7

Fermentation Comparison Acids

Different acids are added to three CO$_2$-regulated bioreactors for a pH shift from 6.95 to 6.8 on day 3. The concentrations of the acid solutions are chosen such that the quantities of substance required, which have been determined beforehand in a titration, are present in 50 ml of solution.

The test set-up is described below:
Platform: Bioreactor/Multifermenter
Method: Fed Batch
Cell: CHO
Seeding density: 3×10$^5$ vc/mL
Start volume: 1.8 L
Run time: 11 days
Medium: Medium B, NaHCO$_3$-free, MOPS-free+Sod-β (25 mM)
Feeding: Feed I continuously from day 2
Temperature: 37° C.
pO$_2$: 60%
Speed: 160 rpm
pH: day 0-3 7.00±0.05, day 3-11 6.80±0.05
pH regulation: NaOH (1.2M) (no CO$_2$)

The different additions to the three fermentation processes are shown in Table 9.

TABLE 9

Experiment plan with different additions.

| run | addition |
|---|---|
| 4.3 | hydrochloric acid 99 mM |
| 4.4 | sulphuric acid 54 mM |
| 4.5 | phosphoric acid 81 mM |

The standardised cell concentrations in FIG. 9A run largely similarly, so that on day 10 the maxima of the individual runs are reached. The cell concentrations of run 4.3 with the addition of hydrochloric acid are constantly below the others.

However, it is noticeable, with respect to the standardised product concentrations (cf. FIG. 9B), that these all run similarly and thus in run 4.3 with the addition of hydrochloric acid the same product concentrations are obtained as in the other processes.

With respect to the lactate concentrations shown in FIG. 9C it is clear that less lactate is produced in the fermentation process as the result of the addition of sulphuric acid (4.4).

Thus the addition of the hydrochloric acid results in a higher productivity of the cells and the addition of the sulphuric acid results in lower lactate concentrations in the fermentation process.

Example 8

Comparison Standard Process with $CO_2$-Regulated Process

In four bioreactors the standard process with the conventional medium B without $CO_2$ regulation and using $Na_2CO_3$ for pH regulation is compared with the $CO_2$-regulated process using medium B, $NaHCO_3$-free, MOPS-free+Sod-β (25 mM) and using NaOH and different acids for the pH regulation.

The test set-up is described below:
Platform: Bioreactor/Multifermenter
Method: Fed Batch
Cell: CHO
Seeding density: $3 \times 10^5$ vc/mL
Start volume: 1.8 L
Run time: 11 days
Feeding: Feed I continuously from day 2
Temperature: 37° C.
$pO_2$: 60%
Speed: 160 rpm
pH: day 0-3 7.00±0.05, day 3-11 6.80±0.05

The different additions to the three fermentation processes are shown in Table 10.

TABLE 10

Experiment plan with different additions.

| Run | Medium | pH regulation | Acid added |
|---|---|---|---|
| 4.1 | Medium B | $Na_2CO_3$ $CO_2$ | — |
| 4.3 | Medium B, $NaHCO_3$-free, MOPS-free + Sod-β (25 mM) | NaOH acid added | hydrochloric acid 99 mM |
| 4.4 | Medium B, $NaHCO_3$-free, MOPS-free + Sod-β (25 mM) | NaOH acid added | sulphuric acid 54 mM |
| 4.5 | Medium B, $NaHCO_3$-free, MOPS-free + Sod-β (25 mM) | NaOH acid added | phosphoric acid 81 mM |

The standardised product concentrations of runs 4.1 and 4.3-4.5 shown in FIG. 10 run in a very similar manner. Almost identical product concentrations are obtained in the standard process (4.1) and in run 4.5 with the addition of phosphoric acid, which means that the $CO_2$-regulated process does not have any disadvantages in terms of the productivity or the product concentration that can be achieved.

Example 9

Comparison $CO_2$ Profiles with Model Cell 2

In five bioreactors the $CO_2$-regulated process using medium B, $NaHCO_3$-free, MOPS-free+Sod-β (25 mM) and the use of NaOH for various $pCO_2$ profiles are compared. The $pCO_2$ is regulated actively by the introduction of $N_2$ and $CO_2$ gas, which can be done by decoupling the pH regulation.

The test set-up is described below:
Platform: Bioreactor/Multifermenter
Method: Fed Batch
Cell: CHO
Seeding density: $3 \times 10^5$ vc/mL
Start volume: 1.8 L
Run time: 11 days
Feeding: Feed I continuously from day 2
Temperature: 37° C.
$pO_2$: 60%
Speed: 160 rpm
pH: day 0-3 7.00±0.05, day 3-11 6.80±0.05

The different $pCO_2$ profiles of the five fermentation processes are shown in Table 11.

TABLE 11

Experiment plan with different $pCO_2$ profiles.

| run | day 0 to day 3 | day 3 to day 7 | day 7 to day 11 |
|---|---|---|---|
| KF1 | 3% | 3% | 3% |
| KF2 | 7% | 3% | 3% |
| KF3 | 11% | 3% | 3% |
| KF4 | 7% | 11% | 7% |
| KF5 | 7% | 11% | 3% |

The standardised live cell concentrations shown in FIG. 11A exhibit significantly better growth characteristics for fermentation run KF1. FIG. 11B for the standardised product concentration also has a better result for KF1. The fermentation period for this experiment was divided into 3 sections, for which the desired values of the $pCO_2$ were varied. The best results were obtained with a continuously low prescribed value for the $pCO_2$ of 3%.

ABBREVIATIONS

The following is a brief explanation of the abbreviations and symbols used in this study.

BI The company Boehringer Ingelheim GmbH & Co. KG

CHO cell Chinese Hamster Ovary cell. A well defined and robust cell line established in 1960 which can also be cultivated in suspension and is often used in drug manufacture.

DoE Design of Experiments. Test planning for optimisation on a mathematical/statistical basis. Software: Modde Downstream Area of the product isolation and enrichment after the time of the cell harvesting. (decrease in volume/concentration).

Feeding Addition of a solution to the fermentation culture which is required by the cells for growth or proliferation.

FS Fermenter control station or fermentation system equ. Equation

TCC Total cell count. Indication of concentration. Number of cells per volume that has been analysed; includes both dead and living cells. Mostly cell density in [Y cells$\times 10^5$/ml].

IPC In-process control. Analysis of parameters while a process is in progress. May form the basis for interventions in the ongoing process, e.g. the addition of a bolus.

LAF Box Laminar-Air-Flow box. Sterile working area.

LCC Live cell count. Indication of concentration. Number of cells per volume that has been analysed as being alive. Mostly cell density in [Y cells$\times 10^5$/ml]. Corresponds to TCC minus number of dead cells.

MFC Mass Flow Controller
MCR Measurement-Control-Regulation; Measurement and regulation technology
Multifermenter A so-called multifermenter is a combined of six identical individual fermenters; for further information see Equipment.
NaHCO₃ Sodium hydrogen carbonate, also (sodium) bicarbonate or soda
PBS Phosphate buffered saline solution which has isotonic properties.
Process format By a process format is meant the setting of the process parameters. It contains time data as well as volume flows of feedings, stirrer speeds etc.
Px P denotes a buffer substance. PA denotes for example buffer substance A. For repetitions of the buffers, PA1, PA2, PA3 etc. are used
Scale-up=scaling or scalability
Increasing the scale of a production plant, usually done with the aid of dimensionless characteristics.
Shake flask (SF) Disposable plastic flask. The lid is provided with a gas-permeable sterile filter and is unscrewed for sampling and feeding.
SDR SensorDish Reader®
Online data capture from a special well plate with measuring dots. Non-invasive tool made by the company Presens of Regensburg.
Titre Indicates the concentration of a product, e.g. a protein such as for example an antibody in [mg/L]. Not to be confused with the conventional meaning of a medical titre.
Upstream Area of cell culture technology starting with the inoculation of the fermenter and fermentation up to the harvesting of the cells. (Increase in volume).
WFI Water for injection. Purified, filtered, desalinated water the quality of which is continuously monitored.
with A medium X with NaCl is for example a medium consisting of all the components for medium X—with an additional defined amount of NaCl.
w/o In the field of the preparation of media, a common abbreviation for "without". A medium X w/o NaCl is for example a medium consisting of all the components for medium X—but without NaCl.
(aq) Index In aqueous solution
d day fermentation day. d0=day of seeding.

The invention claimed is:

1. A method for cultivating eukaryotic cells comprising the following steps:
   a) preparing a eukaryotic host cell which contains a recombinant gene of interest and produces a corresponding product of interest,
   b) cultivating the cell from step a) in a batch-fed fermentation process and in a cell culture medium which contains no $HCO_3^-$ or $CO3^{2-}$ ions, said cell culture medium containing sodium-β-glycerophosphate-pentahydrate ($C_3H_7Na_2O_6P \times 5H_2O$, Sod-β) in an amount effective to act as a buffering agent; and
   c) regulating the pH of the culture medium by means of a non-$CO_2$-forming acid and/or alkaline solution, while the $pCO_2$ of the culture medium is regulated by the introduction of $CO_2$, $O_2$, $N_2$ or air.

2. A bioprocess method of preparing a recombinant product of interest comprising the following steps:
   a) preparing a eukaryotic host cell which contains a recombinant gene of interest and produces a corresponding product of interest,
   b) cultivating the cell from step a) in a batch-fed fermentation process and in a cell culture medium which contains no $HCO_3^-$ or $CO3^{2-}$ ions, said cell culture medium containing sodium-β-glycerophosphate-pentahydrate ($C_3H_7Na_2O_6P \times 5H_2O$, Sod-β) in an amount effective to act as a buffering agent; and
   c) regulating the pH of the culture medium by means of a non-$CO_2$-forming acid and/or alkaline solution, wherein during the bioprocess method the $pCO_2$ in the fermentor is regulated by the introduction of $CO_2$, $O_2$, $N_2$ or air.

3. The method according to claim 2, characterised in that the product of interest is a protein.

4. The method according to claim 1 or 2, characterised in that the $pCO_2$ is regulated by the introduction of $CO_2$ and/or $N_2$ gas.

5. The method according to claim 1 or 2, characterised in that the Sod-β concentration is between 1 mmol/L and 100 mmol/L, or is 5-50 mmol/L, or is 15-30 mmol/L, or is less than or equal to 100 mmol/L or is less than or equal to 25 mmol/L.

6. The method according to claim 1 or 2, characterised in that the acid and/or alkaline solution according to step c) comprises NaOH, HCl, $H_3PO_4$ or $H_2SO_4$.

7. The method according to claim 1 or 2, characterised in that the eukaryotic cell is a mammalian cell.

8. The method according to claim 1 or 2, characterised in that the $pCO_2$ in the initial growth phase is regulated to a value of less than or equal to 10%, or less than or equal to 8%, wherein the initial growth phase is days 0 to 3, or days 1 to 3, or day 1.

9. The method according to claim 1 or 2, characterised in that the $pCO_2$ from day 0 to day 11, or from day 0 to the end of the fermentation is regulated to 3%.

10. The method according to claim 9, characterised in that the $pCO_2$ value is additionally regulated as follows: i) the average $pCO_2$ is less than or equal to 12% in the growth phase, which is days 3-7 or days 4-8, or ii) the $pCO_2$ is greater than or equal to 5%, or 8% or 15%, which is a slightly elevated or high $pCO_2$, in the dying-off phase, which is days 7-11, or days 9-11, or day 7 until the end of the fermentation, or day 9 until the end of the fermentation.

11. A method for culturing eukaryotic cells, comprising the step of culturing the eukaryotic cells in a batch fermentation process and in a cell culture medium which contains no $HCO_3^-$ or $CO3^{2-}$ ions, said cell culture medium containing sodium-β-glycerophosphate-pentahydrate ($C_3H_7Na_2O_6P \times 5H_2O$, Sod-β) in an amount effective to act as a buffering agent, wherein the pH of the culture medium is regulated by means of a non-$CO_2$-forming acid and/or alkaline solution, while the $pCO_2$ of the culture medium is regulated by the introduction of $CO_2$, $O_2$, $N_2$ or air.

* * * * *